US010105442B2

(12) United States Patent
Coppieters et al.

(10) Patent No.: US 10,105,442 B2
(45) Date of Patent: Oct. 23, 2018

(54) TREATMENT OF DIABETES TYPE 1 USING GLP-1 AND ANTI-IL-21

(71) Applicant: Novo Nordisk A/S, Bagsvaerd (DK)

(72) Inventors: Ken Coppieters, Gentofte (DK); Matthias von Herrath, San Diego, CA (US); Tamar Boursalian, Seattle, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/307,592

(22) PCT Filed: May 5, 2015

(86) PCT No.: PCT/EP2015/059811
§ 371 (c)(1),
(2) Date: Oct. 28, 2016

(87) PCT Pub. No.: WO2015/169789
PCT Pub. Date: Nov. 12, 2015

(65) Prior Publication Data
US 2017/0043014 A1    Feb. 16, 2017

Related U.S. Application Data

(60) Provisional application No. 61/989,841, filed on May 7, 2014.

(30) Foreign Application Priority Data

May 23, 2014  (EP) .................................. 14169596
Oct. 21, 2014  (EP) .................................. 14189732

(51) Int. Cl.
*A61K 38/26*        (2006.01)
*A61K 39/395*       (2006.01)
*C07K 16/24*        (2006.01)
*A61K 39/00*        (2006.01)

(52) U.S. Cl.
CPC .......... *A61K 39/3955* (2013.01); *A61K 38/26* (2013.01); *A61K 39/395* (2013.01); *C07K 16/244* (2013.01); *A61K 2039/505* (2013.01)

(58) Field of Classification Search
CPC ............................. A61K 39/395; A61K 38/26
See application file for complete search history.

(56) References Cited

U.S. PATENT DOCUMENTS

| 2004/0052862 A1 | 3/2004 | Henriksen et al. |
| 2006/0160736 A1 | 7/2006 | Nadler |
| 2008/0167226 A1 | 7/2008 | Flink et al. |
| 2009/0191214 A1 | 7/2009 | Jaspers et al. |
| 2014/0178395 A1 | 6/2014 | Rosendahl et al. |
| 2014/0178396 A1 | 6/2014 | Junker et al. |

FOREIGN PATENT DOCUMENTS

| EP | 1841448 A2 | 10/2007 |
| EP | 2746292 A1 | 6/2014 |
| WO | 9808871 A1 | 3/1998 |
| WO | 03028630 A2 | 4/2003 |
| WO | 2003105897 A1 | 12/2003 |
| WO | 2005023291 A2 | 3/2005 |
| WO | 2006074051 A2 | 7/2006 |
| WO | 2006097537 A2 | 9/2006 |
| WO | 2006128083 A2 | 11/2006 |
| WO | 2007016764 A1 | 2/2007 |
| WO | 2007024700 A2 | 3/2007 |
| WO | 2008028914 A1 | 3/2008 |
| WO | 10055366 A2 | 5/2010 |
| WO | 11106558 A1 | 9/2011 |
| WO | 12098113 A1 | 7/2012 |

OTHER PUBLICATIONS

Boettler T et al, Immunotherapy of type 1 diabetes—How to rationally prioritize combination therapies in T1D; International Immunopharmacology, 2010, vol. 10, pp. 1491-1495.
Dubala A et al.Combination of monoclonal antibodies and DPP-IV inhibitors in the treatment of type 1 diabetes: A plausible treatment modality?, Medical hypotheses, 2014, vol. 83, No. 1, pp. 1-5.
Fabrizi et al. IL-21 Is a Major Negative Regulator of IRF4-Dependent Lipolysis Affecting Tregs in Adipose Tissue and Systemic Insulin Sensitivity, Diabetes,2014,vol. 63, pp. 2086-2096.
Grant et al,Testing Agents for Prevention or Reversal of Type 1 Diabetes in Rodents, PLOS One, 2013, vol. 8 , Issue 8, e72989; pp. 1-14.
Hadjiyanni I et al. Exendin-4 Modulates Diabetes Onset in Nonobese Diabetic Mice, Endocrinology, 2008, vol. 149, No. 3, pp. 1338-1349.
Hamming O J et al.Crystal Structure of Interleukin-21 Receptor (IL-21R) Bound to; IL-21 Reveals That Sugar Chain Interacting with WSXWS Motif Is Integral Part of IL-21R, The Journal of biological Chemistry, 2012, vol. 287, No. 12, pp. 9454-9460.
McGuire H M et al,Interleukin-21 Is Critically Required in Autoimmune and Allogeneic Responses to Islet Tissue in Murine Models, Diabetes, 2011, vol. 60, No. 3, pp. 867-875.
Ogawa N. et al.Cure of Overt Diabetes in NOD Mice by Transient Treatment With Anti-Lymphocyte Serum and Exendin-4, Diabetes, 2004, vol. 53, pp. 1700-1705.
Rother et al.Effects of Exenatide Alone and in Combination With Daclizumab on-beta Cell Function in Long-Standing Type 1 Diabetes, Diabetes Care, 2009, vol. 32, pp. 2251-2257.
Sherry N A et al.Exendin-4 Improves Reversal of Diabetes in NOD Mice Treated with Anti-CD3 Monoclonal Antibody by Enhancing Recovery of beta Cells, Endocrinology, 2007,vol. 148 No. 11, pp. 5136-5144.

(Continued)

*Primary Examiner* — Gyan Chandra
(74) *Attorney, Agent, or Firm* — Jianjie Hu

(57) ABSTRACT

The present invention relates to use of a GLP-1 agonist and an anti-IL-2 antibody in treatment and/or prevention of type 1 diabetes.

15 Claims, 5 Drawing Sheets
Specification includes a Sequence Listing.

(56) References Cited

OTHER PUBLICATIONS

Spolski R et al. Interleukin-21: a double-edged sword with therapeutic potential, Nature Reviews Drug Discovery. 2014 vol. 13, No. 5, pp. 379-395.
Spolski R et al.IL-21 signaling is critical for the development of type I diabetes in the NOD mouse. Proceedings of the National Academy of Sciences of the United States of America, 2008,vol. 105, No. 37.pp. 14028-14033.
Wang T et al.Functional Characterization of a Nonmammalian IL-21:Rainbow Trout *Oncorhynchus mykiss* IL-21 Upregulates the Expression of the Th Cell Signature Cytokines IFN-g, IL-10,and IL-22, Journal of Immunology,2011, vol. 186, No. 2 pp. 708-721.
Yang et al., Combined treatment with lisofylline and exendin-4 reverses autoimmune diabetes, Biochemical and Biophysical Research Communication 2006, vol. 344, pp. 1017-1022.

A

B

SEQUENCE LISTING

```
<160> NUMBER OF SEQ ID NOS: 27

<210> SEQ ID NO 1
<211> LENGTH: 162
<212> TYPE: PRT
<213> ORGANISM: homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 213
<212> TYPE: PRT
<213> ORGANISM: artificial
<220> FEATURE:
<223> OTHER INFORMATION: "mAb 5", light chain

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Trp Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 3
<211> LENGTH: 456
<212> TYPE: PRT
<213> ORGANISM: artificial
<220> FEATURE:
<223> OTHER INFORMATION: "mAb 5", heavy chain of the IgG1 isotype

<400> SEQUENCE: 3

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Phe Ile Trp Tyr Asp Gly Ser Asp Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Asp Ser Ser Asp Trp Tyr Gly Asp Tyr Tyr Phe Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Glu Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ser Ser Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 4
<211> LENGTH: 214
<212> TYPE: PRT
<213> ORGANISM: artificial
<220> FEATURE:
<223> OTHER INFORMATION: "mAb 14", light chain

<400> SEQUENCE: 4

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Asp Ser Ala
                20                  25                  30

Leu Ala Trp Tyr Gln Gln Lys Pro Gly Lys Ala Pro Lys Ile Leu Ile
            35                  40                  45

His Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 5
<211> LENGTH: 447
<212> TYPE: PRT
<213> ORGANISM: artificial
<220> FEATURE:
<223> OTHER INFORMATION: "mAb 14" heavy chain of the IgG4 isotype

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Ser Tyr
            20                  25                  30

Ser Met Asn Trp Val Arg Gln Ala Pro Gly Lys Gly Leu Glu Trp Val
            35                  40                  45

Ser Ser Ile Thr Ser Gly Ser Tyr Tyr Ile His Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Arg Gly Trp Gly Tyr Tyr Gly Met Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

```
Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
    435                 440                 445

<210> SEQ ID NO 6
<211> LENGTH: 538
<212> TYPE: PRT
<213> ORGANISM: homo sapiens

<400> SEQUENCE: 6

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160
```

```
Arg Asn Arg Gly Asp Pro Trp Ala Val Ser Pro Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
            210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
            325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
            405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
530                 535
```

<210> SEQ ID NO 7
<211> LENGTH: 369
<212> TYPE: PRT
<213> ORGANISM: homo sapiens

```
<400> SEQUENCE: 7

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
            210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
            290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
            355                 360                 365

Thr

<210> SEQ ID NO 8
<211> LENGTH: 31
<212> TYPE: PRT
<213> ORGANISM: homo sapiens
```

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

```
<210> SEQ ID NO 9
<211> LENGTH: 40
<212> TYPE: PRT
<213> ORGANISM: Artificial Sequence
<220> FEATURE:
<223> OTHER INFORMATION: Artificial sequence based on human GLP-1
<220> FEATURE:
<221> NAME/KEY: MISC_FEATURE
<222> LOCATION: (1)..(1)
<223> OTHER INFORMATION: L-histidine, D-histidine, desamino-histidine,
      2-amino-histidine, alpha-hydroxy-histidine, homohistidine,
      N-alpha-acetyl-histidine, alpha-fluoromethyl-histidine,
      alpha-methyl-histidine, 3-pyridylalanine, 2-pyridylalanine or
      4-pyridylalanine
<220> FEATURE:
<221> NAME/KEY: MISC_FEATURE
<222> LOCATION: (2)..(2)
<223> OTHER INFORMATION: Ala, Gly, Val, Leu, Ile, Lys,
      Aib,(1-aminocyclopropyl) carboxylic acid,(1- aminocyclobutyl)
      carboxylic acid, (1-aminocyclopentyl) carboxylic acid,
      (1-aminocyclohexyl) carboxylic acid, (1-aminocycloheptyl)
      carboxylic acid, or (1-aminocyclooctyl)
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser, Lys or Arg
<220> FEATURE:
<221> NAME/KEY: MISC_FEATURE
<222> LOCATION: (13)..(13)
<223> OTHER INFORMATION: Tyr or Gln
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (16)..(16)
<223> OTHER INFORMATION: Gly, Glu or Aib
<220> FEATURE:
<221> NAME/KEY: MISC_FEATURE
<222> LOCATION: (17)..(17)
<223> OTHER INFORMATION: Gln, Glu, Lys or Arg
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Lys, Glu or Arg
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala, Glu or Arg
<220> FEATURE:
<221> NAME/KEY: MISC_FEATURE
<222> LOCATION: (27)..(27)
<223> OTHER INFORMATION: Val or Lys
<220> FEATURE:
<221> NAME/KEY: MISC_FEATURE
<222> LOCATION: (28)..(28)
<223> OTHER INFORMATION: Lys, Glu, Asn or Arg
```

```
<220> FEATURE:
<221> NAME/KEY: MISC_FEATURE
<222> LOCATION: (29)..(29)
<223> OTHER INFORMATION: Gly or Aib
<220> FEATURE:
<221> NAME/KEY: MISC_FEATURE
<222> LOCATION: (30)..(30)
<223> OTHER INFORMATION: Arg, Gly or Lys
<220> FEATURE:
<221> NAME/KEY: MISC_FEATURE
<222> LOCATION: (31)..(31)
<223> OTHER INFORMATION: Gly, Ala, Glu, Pro, Lys, amide or is absent;
      provided that if absent then each amino acid residue downstream
      is also absent
<220> FEATURE:
<221> NAME/KEY: MISC_FEATURE
<222> LOCATION: (32)..(32)
<223> OTHER INFORMATION: Lys, Ser, amide or is absent; provided that if
      absent then each amino acid residue downstream is also absent
<220> FEATURE:
<221> NAME/KEY: MISC_FEATURE
<222> LOCATION: (33)..(33)
<223> OTHER INFORMATION: Ser, Lys, amide or is absent; provided that if
      absent then each amino acid residue downstream is also absent
<220> FEATURE:
<221> NAME/KEY: MISC_FEATURE
<222> LOCATION: (34)..(34)
<223> OTHER INFORMATION: Gly, amide or is absent; provided that if
      absent then each amino acid residue downstream is also absent
<220> FEATURE:
<221> NAME/KEY: MISC_FEATURE
<222> LOCATION: (35)..(35)
<223> OTHER INFORMATION: Ala, amide or is absent; provided that if
      absent then each amino acid residue downstream is also absent
<220> FEATURE:
<221> NAME/KEY: MISC_FEATURE
<222> LOCATION: (36)..(36)
<223> OTHER INFORMATION: Pro, amide or is absent; provided that if
      absent then each amino acid residue downstream is also absent
<220> FEATURE:
<221> NAME/KEY: MISC_FEATURE
<222> LOCATION: (37)..(37)
<223> OTHER INFORMATION: Pro, amide or is absent; provided that if
      absent then each amino acid residue downstream is also absent
<220> FEATURE:
<221> NAME/KEY: MISC_FEATURE
<222> LOCATION: (38)..(38)
<223> OTHER INFORMATION: Pro, amide or is absent; provided that if
      absent then each amino acid residue downstream is also absent
<220> FEATURE:
<221> NAME/KEY: MISC_FEATURE
<222> LOCATION: (39)..(39)
<223> OTHER INFORMATION: Ser, amide or is absent; provided that if
      absent then each amino acid residue downstream is also absent
<220> FEATURE:
<221> NAME/KEY: MISC_FEATURE
<222> LOCATION: (40)..(40)
<223> OTHER INFORMATION: amide or is absent; provided that if absent
      then each amino acid residue downstream is also absent

<400> SEQUENCE: 9

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa Xaa
        35                  40

<210> SEQ ID NO 10
<211> LENGTH: 32
<212> TYPE: PRT
<213> ORGANISM: Artificial Sequence
<220> FEATURE:
<223> OTHER INFORMATION: Artificial sequence based on human GLP-1
<220> FEATURE:
```

```
<221> NAME/KEY: MISC_FEATURE
<222> LOCATION: (1)..(1)
<223> OTHER INFORMATION: L-histidine, D-histidine, desamino-histidine,
      2-amino-histidine,-hydroxy-histidine, homohistidine,
      N-alpha-acetyl-histidine, alpha-fluoromethyl-histidine,
      alpha-methyl-histidine, 3-pyridylalanine, 2-pyridylalanine or
<220> FEATURE:
<221> NAME/KEY: MISC_FEATURE
<222> LOCATION: (2)..(2)
<223> OTHER INFORMATION: Ala, Gly, Val, Leu, lle, Lys, Aib,
      (1-aminocyclopropyl) carboxylic acid, (1- aminocyclobutyl)
      carboxylic acid, (1-aminocyclopentyl) carboxylic acid,
      (1-aminocyclohexyl) carboxylic acid,(1-aminocycloheptyl)
      carboxylic acid,or
<220> FEATURE:
<221> NAME/KEY: MISC_FEATURE
<222> LOCATION: (12)..(12)
<223> OTHER INFORMATION: Ser, Lys or Arg
<220> FEATURE:
<221> NAME/KEY: MISC_FEATURE
<222> LOCATION: (16)..(16)
<223> OTHER INFORMATION: Gly, Glu or Aib
<220> FEATURE:
<221> NAME/KEY: MISC_FEATURE
<222> LOCATION: (17)..(17)
<223> OTHER INFORMATION: Gln, Glu, Lys or Arg
<220> FEATURE:
<221> NAME/KEY: MISC_FEATURE
<222> LOCATION: (20)..(20)
<223> OTHER INFORMATION: Lys, Glu or Arg
<220> FEATURE:
<221> NAME/KEY: MISC_FEATURE
<222> LOCATION: (24)..(24)
<223> OTHER INFORMATION: Ala, Glu or Arg
<220> FEATURE:
<221> NAME/KEY: MISC_FEATURE
<222> LOCATION: (28)..(28)
<223> OTHER INFORMATION: Lys, Glu or Arg
<220> FEATURE:
<221> NAME/KEY: MISC_FEATURE
<222> LOCATION: (29)..(29)
<223> OTHER INFORMATION: Gly or Aib
<220> FEATURE:
<221> NAME/KEY: MISC_FEATURE
<222> LOCATION: (30)..(30)
<223> OTHER INFORMATION: Arg or Lys
<220> FEATURE:
<221> NAME/KEY: MISC_FEATURE
<222> LOCATION: (31)..(31)
<223> OTHER INFORMATION: Gly, Ala, Glu or Lys
<220> FEATURE:
<221> NAME/KEY: MISC_FEATURE
<222> LOCATION: (32)..(32)
<223> OTHER INFORMATION: Lys, amide or is absent

<400> SEQUENCE: 10

Xaa Xaa Glu Gly Thr Phe Thr Ser Asp Val Ser Xaa Trp Leu Glu Xaa
1               5                   10                  15

Xaa Ala Ala Xaa Glu Phe Ile Xaa Trp Leu Val Xaa Xaa Xaa Xaa Xaa
            20                  25                  30

<210> SEQ ID NO 11
<211> LENGTH: 130
<212> TYPE: PRT
<213> ORGANISM: Artificial Sequence
<220> FEATURE:
<223> OTHER INFORMATION: Recombinant mouse IL-21

<400> SEQUENCE: 11

Met His Lys Ser Ser Pro Gln Gly Pro Asp Arg Leu Leu Ile Arg Leu
1               5                   10                  15

Arg His Leu Ile Asp Ile Val Glu Gln Leu Lys Ile Tyr Glu Asn Asp
            20                  25                  30
```

```
Leu Asp Pro Glu Leu Leu Ser Ala Pro Gln Asp Val Lys Gly His Cys
         35                  40                  45

Glu His Ala Ala Phe Ala Cys Phe Gln Lys Ala Lys Leu Lys Pro Ser
     50                  55                  60

Asn Pro Gly Asn Asn Lys Thr Phe Ile Ile Asp Leu Val Ala Gln Leu
 65                  70                  75                  80

Arg Arg Arg Leu Pro Ala Arg Arg Gly Gly Lys Lys Gln Lys His Ile
                 85                  90                  95

Ala Lys Cys Pro Ser Cys Asp Ser Tyr Glu Lys Arg Thr Pro Lys Glu
            100                 105                 110

Phe Leu Glu Arg Leu Lys Trp Leu Leu Gln Lys Met Ile His Gln His
        115                 120                 125

Leu Ser
    130

<210> SEQ ID NO 12
<211> LENGTH: 128
<212> TYPE: PRT
<213> ORGANISM: Artificial Sequence
<220> FEATURE:
<223> OTHER INFORMATION: VL amino acid sequence of mouse surrogate
      anti-IL-21 is an mIgG1/kappa isotype

<400> SEQUENCE: 12

Met Asp Phe Gln Val Gln Ile Phe Ser Phe Leu Leu Ile Ser Ala Ser
 1               5                  10                  15

Val Ile Leu Ser Arg Gly Gln Thr Val Leu Ile Gln Ser Pro Ala Ile
             20                  25                  30

Met Ser Ala Ser Pro Gly Glu Lys Val Thr Met Thr Cys Ser Ala Ser
         35                  40                  45

Ser Ser Val Ser Tyr Met His Trp Tyr Gln Gln Lys Ser Gly Thr Ser
     50                  55                  60

Pro Lys Arg Trp Ile Tyr Asp Thr Ser Lys Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Ser Met Glu Ala Glu Asp Ala Ala Thr Tyr Tyr Cys Gln Gln Trp
            100                 105                 110

Asn Ser Asn Pro Pro Thr Phe Gly Gly Gly Thr Lys Leu Glu Met Lys
        115                 120                 125

<210> SEQ ID NO 13
<211> LENGTH: 144
<212> TYPE: PRT
<213> ORGANISM: Artificial Sequence
<220> FEATURE:
<223> OTHER INFORMATION: VH amino acid sequence of mouse surrogate
      anti-IL-21 is an mIgG1/kappa isotype

<400> SEQUENCE: 13

Met Asn Phe Gly Pro Ser Leu Ile Phe Leu Val Leu Ile Leu Lys Gly
 1               5                  10                  15

Val Gln Cys Glu Val Gln Leu Val Glu Ser Gly Gly Gly Leu Val Lys
             20                  25                  30

Pro Gly Gly Ser Leu Lys Leu Ser Cys Ala Ala Ser Gly Phe Thr Phe
         35                  40                  45

Asn Arg Tyr Ser Met Ser Trp Val Arg Gln Ser Pro Glu Lys Arg Leu
     50                  55                  60
```

Glu Trp Val Ala Glu Ile Ser Val Gly Gly Ser Tyr Thr Gln Tyr Val
65                  70                  75                  80

Asp Ile Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Arg Leu Tyr Tyr Ser Gly Ser Gly Asp Ser Tyr Tyr
        115                 120                 125

Tyr Ala Met Asp Tyr Trp Gly Gln Gly Thr Ser Val Thr Val Ser Ser
    130                 135                 140

<210> SEQ ID NO 14
<211> LENGTH: 145
<212> TYPE: PRT
<213> ORGANISM: artificial
<220> FEATURE:
<223> OTHER INFORMATION: Part of anti-IL-21 antibody

<400> SEQUENCE: 14

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Phe Ile Trp Tyr Asp Gly Ser Asp Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Gly Asp Ser Ser Asp Trp Tyr Gly Asp Tyr
        115                 120                 125

Tyr Phe Gly Met Asp Val Trp Gly Gln Gly Thr Thr Val Thr Val Ser
    130                 135                 140

Ser
145

<210> SEQ ID NO 15
<211> LENGTH: 5
<212> TYPE: PRT
<213> ORGANISM: artificial
<220> FEATURE:
<223> OTHER INFORMATION: Part of anti-IL-21 antibody

<400> SEQUENCE: 15

Ser Tyr Gly Met His
1               5

<210> SEQ ID NO 16
<211> LENGTH: 17
<212> TYPE: PRT
<213> ORGANISM: artificial
<220> FEATURE:
<223> OTHER INFORMATION: Part of anti-IL-21 antibody

<400> SEQUENCE: 16

Phe Ile Trp Tyr Asp Gly Ser Asp Lys Tyr Tyr Ala Asp Ser Val Lys

```
1               5                  10                  15
Gly

<210> SEQ ID NO 17
<211> LENGTH: 17
<212> TYPE: PRT
<213> ORGANISM: artificial
<220> FEATURE:
<223> OTHER INFORMATION: Part of anti-IL-21 antibody

<400> SEQUENCE: 17

Asp Gly Asp Ser Ser Asp Trp Tyr Gly Asp Tyr Tyr Phe Gly Met Asp
1               5                  10                  15
Val

<210> SEQ ID NO 18
<211> LENGTH: 126
<212> TYPE: PRT
<213> ORGANISM: artificial
<220> FEATURE:
<223> OTHER INFORMATION: Part of anti-IL-21 antibody

<400> SEQUENCE: 18

Met Glu Thr Pro Ala Gln Leu Leu Phe Leu Leu Leu Trp Leu Pro
1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Trp Thr Phe Gly Gln Gly Thr Lys Val Glu Ile Lys
        115                 120                 125

<210> SEQ ID NO 19
<211> LENGTH: 12
<212> TYPE: PRT
<213> ORGANISM: artificial
<220> FEATURE:
<223> OTHER INFORMATION: Part of anti-IL-21 antibody

<400> SEQUENCE: 19

Arg Ala Ser Gln Ser Val Ser Ser Ser Tyr Leu Ala
1               5                  10

<210> SEQ ID NO 20
<211> LENGTH: 7
<212> TYPE: PRT
<213> ORGANISM: artificial
<220> FEATURE:
<223> OTHER INFORMATION: Part of anti-IL-21 antibody

<400> SEQUENCE: 20

Gly Ala Ser Ser Arg Ala Thr
1               5
```

```
<210> SEQ ID NO 21
<211> LENGTH: 7
<212> TYPE: PRT
<213> ORGANISM: artificial
<220> FEATURE:
<223> OTHER INFORMATION: Part of anti-IL-21 antibody

<400> SEQUENCE: 21

Gln Gln Tyr Gly Ser Trp Thr
1               5

<210> SEQ ID NO 22
<211> LENGTH: 5
<212> TYPE: PRT
<213> ORGANISM: artificial
<220> FEATURE:
<223> OTHER INFORMATION: Synthetic sequence

<400> SEQUENCE: 22

Thr Tyr Gly Met His
1               5

<210> SEQ ID NO 23
<211> LENGTH: 39
<212> TYPE: PRT
<213> ORGANISM: Artificial Sequence
<220> FEATURE:
<223> OTHER INFORMATION: Synthetic sequence

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 32
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (3)..(3)
<223> OTHER INFORMATION: Xaa is 2-aminoisobutyric acid
<220> FEATURE:
<221> NAME/KEY: MISC_FEATURE
<222> LOCATION: (31)..(31)
<223> OTHER INFORMATION: Xaa is 2-aminoisobutyric acid

<400> SEQUENCE: 24

His Ala Xaa Glu Gly Thr Phe Thr Ser Asp Val Ser Ser Tyr Leu Glu
1               5                   10                  15

Gly Gln Ala Ala Lys Glu Phe Ile Ala Trp Leu Val Lys Ala Xaa Arg
            20                  25                  30

<210> SEQ ID NO 25
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 25
```

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg
    50                  55                  60

<210> SEQ ID NO 26
<211> LENGTH: 128
<212> TYPE: PRT
<213> ORGANISM: Artificial Sequence
<220> FEATURE:
<223> OTHER INFORMATION: Synthetic Sequence

<400> SEQUENCE: 26

Met Asp Phe Gln Val Gln Ile Phe Ser Phe Leu Leu Ile Ser Ala Ser
1               5                   10                  15

Val Ile Leu Ser Arg Gly Gln Thr Val Leu Ile Gln Ser Pro Ala Ile
            20                  25                  30

Met Ser Ala Ser Pro Gly Glu Lys Val Thr Met Thr Cys Ser Ala Ser
            35                  40                  45

Ser Ser Val Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Asn Ser Asn Pro Pro Thr Phe Gly Gly Gly Thr Lys Leu Glu Met Lys
        115                 120                 125

<210> SEQ ID NO 27
<211> LENGTH: 144
<212> TYPE: PRT
<213> ORGANISM: Artificial Sequence
<220> FEATURE:
<223> OTHER INFORMATION: Synthetic Sequence

<400> SEQUENCE: 27

Met Asn Phe Gly Pro Ser Leu Ile Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Asn Arg Tyr Ser Met Ser Trp Val Arg Gln Ser Pro Glu Lys Arg Leu
    50                  55                  60

Glu Trp Val Ala Glu Ile Ser Val Gly Gly Ser Tyr Thr Gln Tyr Val
65                  70                  75                  80

Asp Ile Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Arg Leu Tyr Tyr Ser Gly Ser Gly Asp Ser Tyr Tyr
        115                 120                 125

```
Tyr Ala Met Asp Tyr Trp Gly Gln Gly Thr Ser Val Thr Val Ser Ser
    130                 135                 140
```

TREATMENT OF DIABETES TYPE 1 USING GLP-1 AND ANTI-IL-21

CROSS-REFERENCE TO RELATED APPLICATIONS

This application is a 35 U.S.C. § 371 National Stage application of International Application PCT/EP2015/059811 (published as WO 2015/169789), filed May 5, 2015, which claimed priority of European Patent Applications 14169596.5, filed May 23, 2014, and 14189732.2, filed Oct. 21, 2014; this application further claims priority under 35 U.S.C. § 119 of U.S. Provisional Application 61/989,841, filed May 7, 2014, the contents thereof which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 11, 2016, is named 140039US02_SeqList.txt and is 35 kilobytes in size.

The present invention relates to use of a GLP-1 agonist, such as a GLP-1 peptide, and an anti-IL-21 antibody in type 1 diabetes.

BACKGROUND

Although advances in exogenous insulin therapy have enabled subjects with type 1 diabetes to adequately control their metabolic disturbances, there are still no treatment options that tackle its underlying cause. There is thus a need for improved treatments and options for prevention of type 1 diabetes.

IL-21 has a four helix bundle structure (helix 1-4/A-D—as defined e.g. in FIG. 1 in: J. Immunol., 2011 vol. 186 no. 2, p. 708-721), arranged in an up-up-down-down topology typical for the class I cytokines. IL-21 signals through a heterodimeric receptor complex, consisting of the private chain IL-21Rα (also referred to as IL-21R) and the γC/IL-2Rγ/common gamma chain the latter being shared by IL-2, IL-4, IL-7, IL-9, and IL-15. γC and IL-21Rα bind to non-overlapping binding sites on IL-21-IL-21Rα binds to helix 1+3 and γC binds to helix 2+4 on human IL-21. IL-21Rα binds IL-21 with high affinity and provides the majority of the binding energy. However, interaction with γC is required for signalling and IL-21 mutants which bind IL-21Rα but fail to interact properly with γC are potent antagonists of IL-21 signalling. IL-21 exerts pleiotropic effects on both innate and adaptive immune responses. It is mainly produced by activated CD4+ T cells, follicular T cells and Natural killer T cells. The amino acid sequence of human IL-21 is shown in SEQ ID NO 1. IL-21 antagonism has been suggested as a possible route for treatment of inflammation due to IL-21 multiple roles in stimulation of the immune system. Further details about IL-21/IL-21Rα binding are described in JBC, VOL. 287, NO. 12, pp. 9454-9460, Mar. 16, 2012 and examplatory anti-IL-21 antibodies are described in WO2010055366 and WO2012098113.

Glucagon-Like Peptide-1 (GLP-1) is a well-studied peptide for it's role in glucose metabolisme. The active forms of human GLP-1 is referred to as GLP-1(7-37) and GLP-1-(7-36)NH2 as the first 6 amino acid residues are removed during maturation. The peptide is very short lived and is a potent anti-hyperglycemic hormone capable of stimulating glucose-dependent insulin secretion and suppressing glucagon secretion. Therapeutic compounds for use in Type 2 diabetes treatment agonising the action of GLP-1 includes liraglutide, exenatide, lixisenatide, albiglutide and dulaglutide.

SUMMARY

The present invention concerns the combined effect of administration of an IL-21 inhibitor and a GLP-1 agonist, which as described herein is found to helpful in the treatment and prevention of type 1 diabetes.

In some embodiments the invention relates to use of a GLP-1 agonist, such as a GLP-1 peptide, and an inhibitor of IL-21 function for the treatment and/or prevention of type 1 diabetes. In some embodiments the invention relates to a method for the treatment and/or prevention of type 1 diabetes comprising administration of a GLP-1 agonist, such as a GLP-1 peptide, and an inhibitor of IL-21 function to a patient in need thereof. In one embodiment the invention relates to a GLP-1 agonist and an inhibitor of IL-21 function for use in a method of treatment and/or prevention of type 1 diabetes.

In one embodiment the invention relates to a GLP-1 agonist and an inhibitor of IL-21 function for use in manufacturing of one or more medicaments for treatment and/or prevention of type 1 diabetes.

The method according to the invention may in an embodiment comprise administering effective amounts of a GLP-1 agonist and an inhibitor of IL-21 function to a subject in need. In one embodiment the subject is a recently diagnosed type 1 diabetes patients, that preferably retains some production of endogenous insulin. The combined treatment with a GLP-1 agonist and an inhibitor of IL-21 function allows the patient to avoid or reduce the need for exogenous insulin therapy. The combined treatment with a GLP-1 agonist and an inhibitor of IL-21 function in an embodiment preserves beta-cell function compared to standard treatment with exogenous insulin.

For each of the treatment regimens the number of animals were 10 per group at onset of experiment, however, over the course of the experiment, some animals were removed from the study and euthanized due to high blood glucose values (above 600 mg/dL) and/or poor general health; euthanized animals are indicated by "*". For FIG. 1 lower graph and 2 lower graph, the time period shown runs through the liraglutide treatment phase (days 0-35 post diabetes onset) and an additional 35 days of monitoring (indicated by "withdraw liraglutide").

Figure 1:
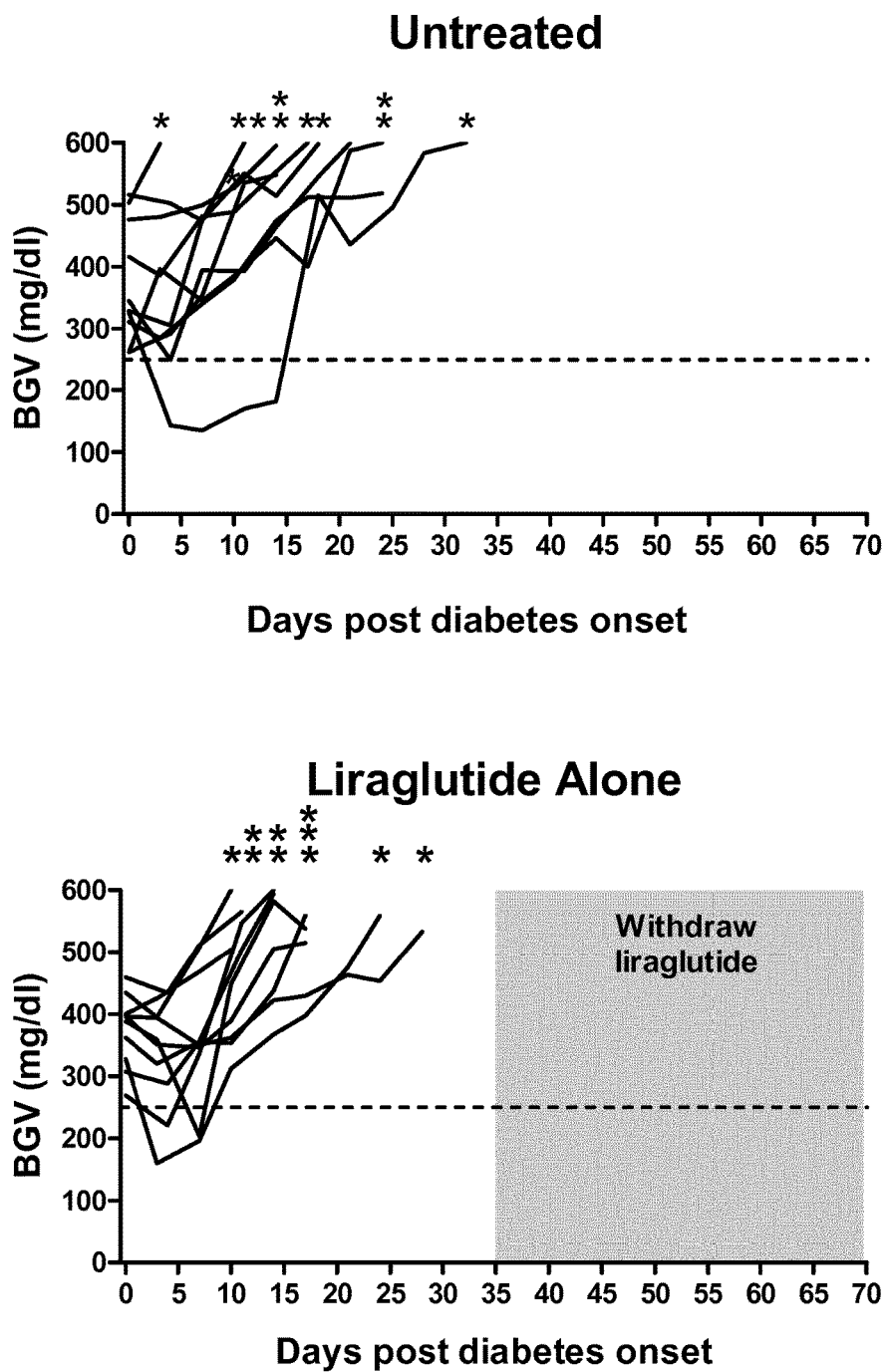
FIG. 1 shows blood glucose (BGV) over time in the NOD model for individual untreated control animals (upper graph) and individual animals following administration of liraglutide (lower graph).
Figure 2:
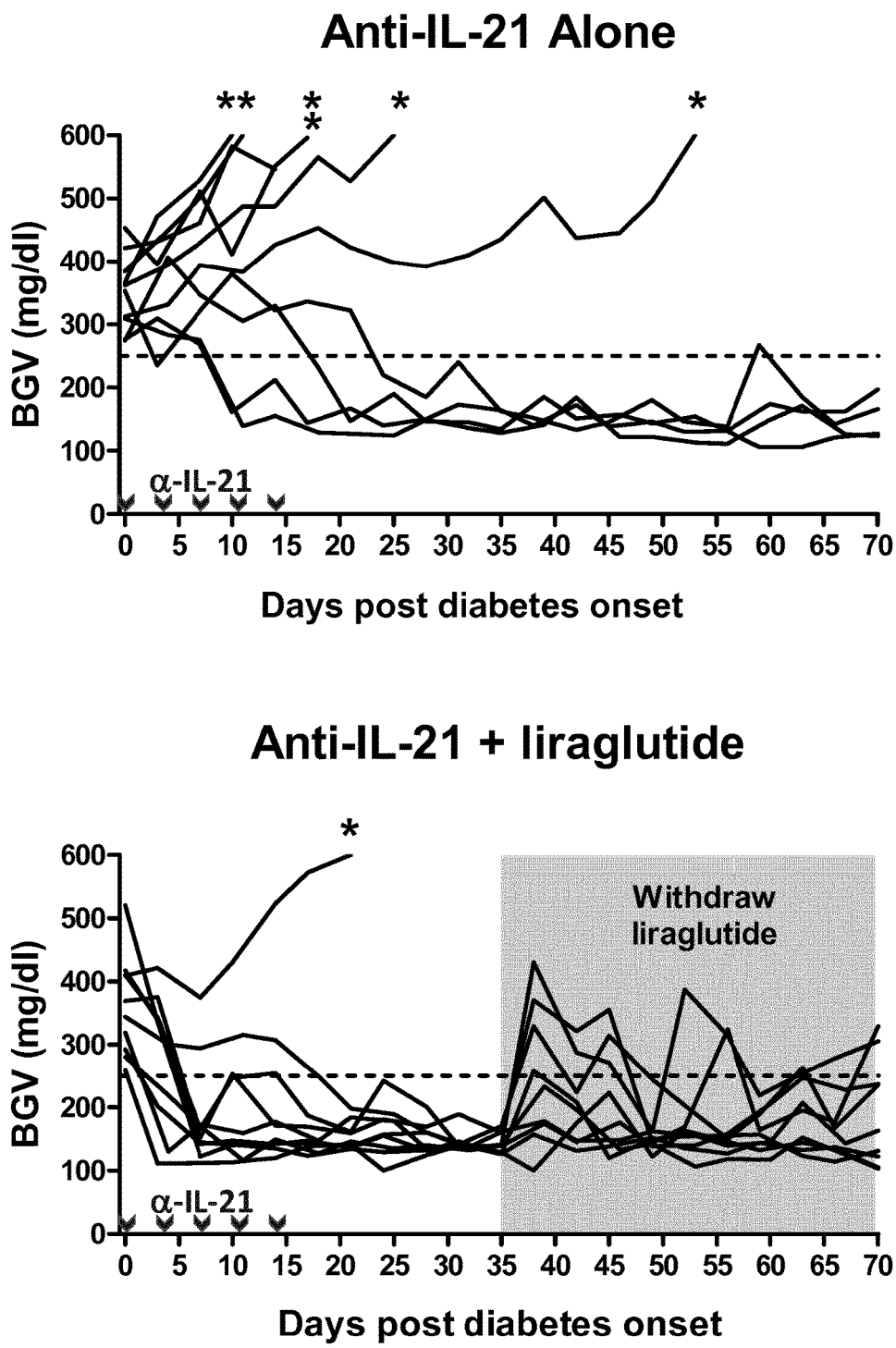
FIG. 2 shows blood glucose (BGV) over time in the NOD model for individual animals following administration of anti-IL-21 antibody (upper graph) and individual animals following administration of liraglutide and anti-IL-21 antibody (lower graph).
Figure 3:
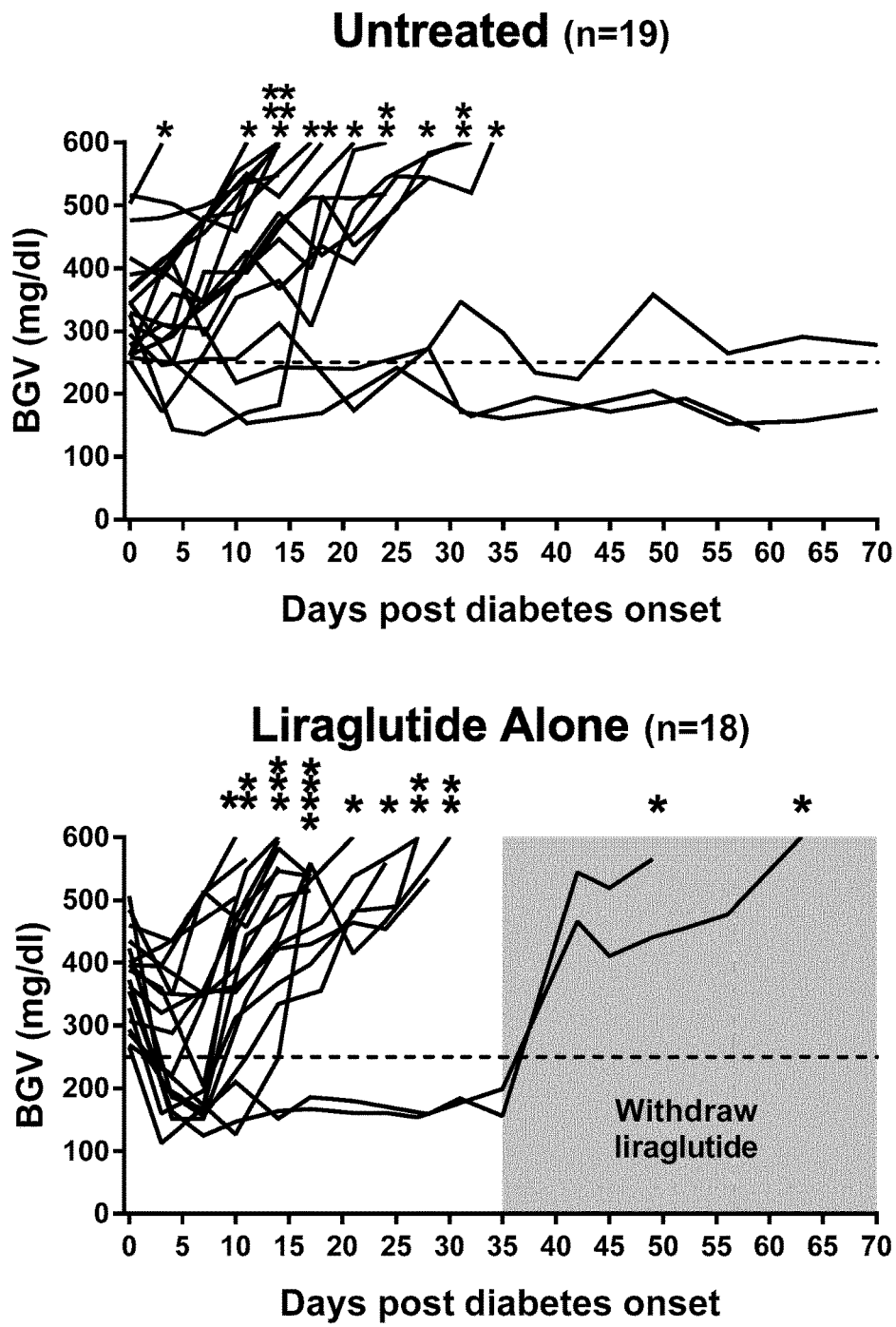
Figure 4:
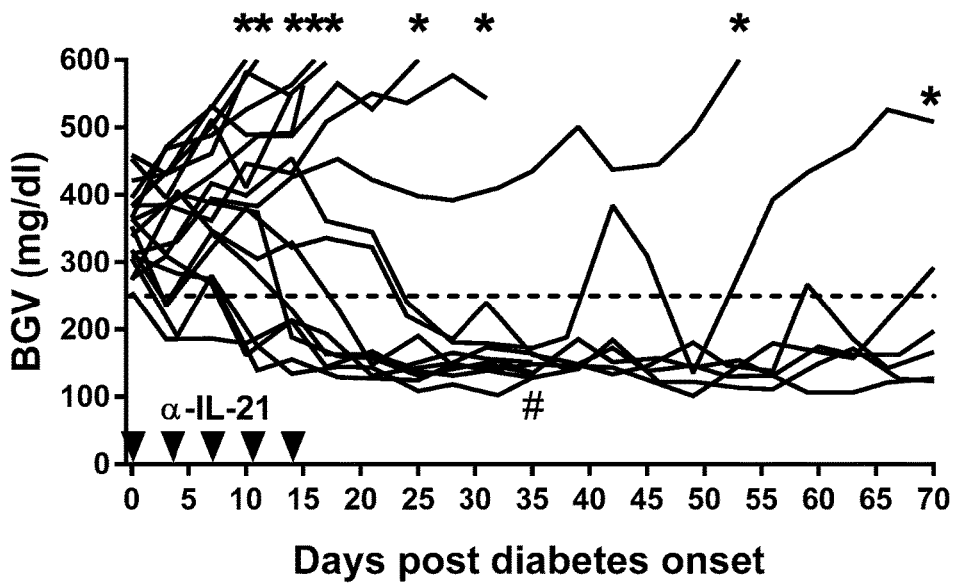
Figure 4:
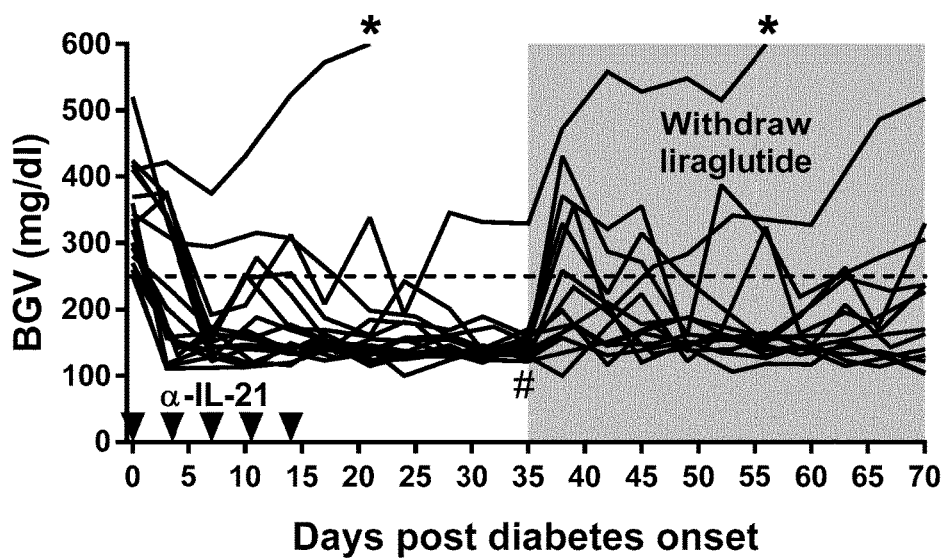

FIG. 3 and FIG. 4 are similar to FIGS. 1 and 2 but include all animals enrolled in the study described in examples 1 and 2. On FIG. 4 the "#" at day 35 signifies that 3 mice from each of the anti-IL-21 and combination treatment groups were sacrificed for other purpose (histology evaluation) and were thus not monitored further.

Figure 5:
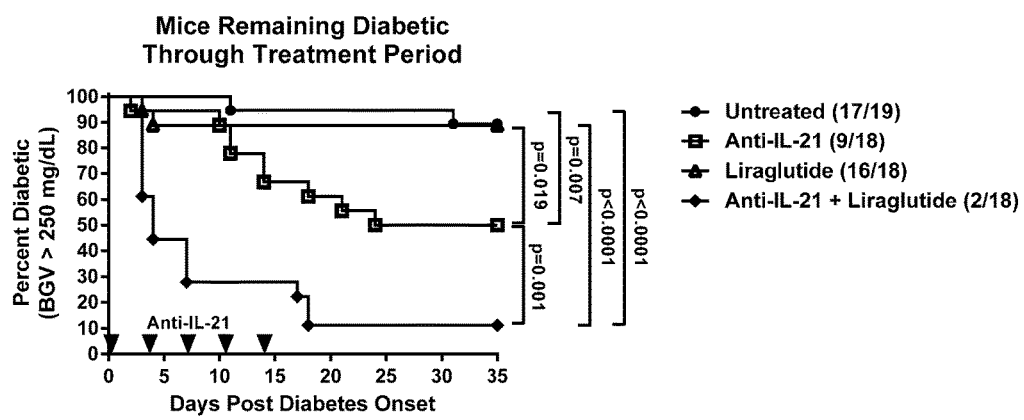
Figure 5:
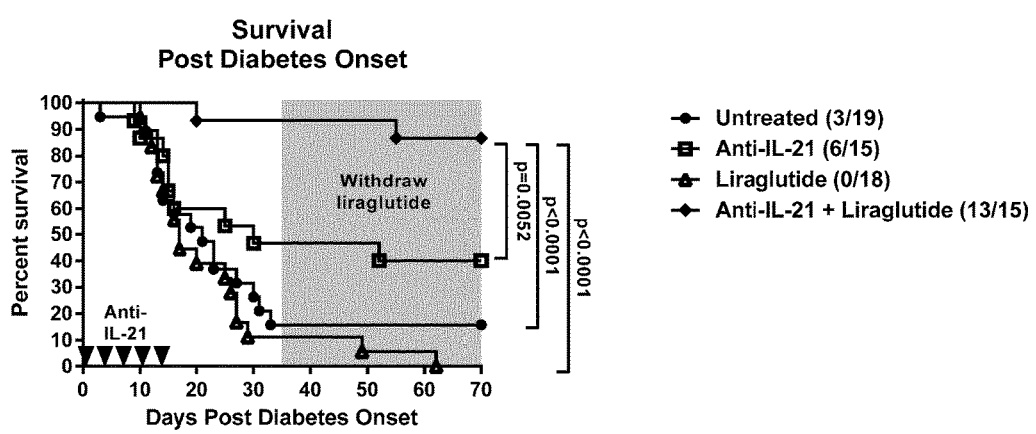

FIG. 5 Kaplan-Meier plots—diabetes incidence and survival rate

Data from Example 1 and 2 are compiled. Liraglutide was administered daily for 35 days. Timing of anti-IL-21 administrations is marked by a triangle/arrow on the X-axes. Statistical significance was determined by log-rank Mantel-cox test. P values are only shown for comparisons that had significant differences. All other comparisons were not significant. Three animals from the Anti-IL-21 monotherapy group as well as three mice from the combination group were sacrificed at day 35 for histological analysis and were not included in the day 70 survival analysis. A. Proportion of mice remaining diabetic through treatment period. B. "Survival" through 70 days post diabetes onset. Survival is defined as those animals that did not become terminally hyperglycemic (BGV≥600 mg/dl for 2 consecutive days). Shaded area indicates withdrawal of liraglutide. The total number of mice in treatment groups 3 and 4 is only 15 per group (and not 18) due to the 3 mice removed for histology.

DESCRIPTION

The present inventors surprisingly found that administration of a GLP-1 agonist, such as a GLP-1 peptide, and an inhibitor of IL-21 function provides improved control of blood glucose levels in diabetic subjects, such as a lasting normalization of blood glucose levels in diabetic subjects.

The present invention relates to use of a GLP-1 agonist, such as a GLP-1 peptide, and an inhibitor of IL-21 function for the treatment and/or prevention of type 1 diabetes. In other words, the present invention relates to a method for the treatment and/or prevention of type 1 diabetes comprising administration of a GLP-1 agonist, such as a GLP-1 peptide, and an inhibitor of IL-21 function to a patient in need thereof.

In one embodiment the GLP-1 agonist, such as a GLP-1 peptide, and the inhibitor of IL-21 function are for use in a method for treatment or prevention of type 1 diabetes.

In one embodiment the GLP-1 agonist, such as a GLP-1 peptide, and the inhibitor of IL-21 function are administered to a subject with recently diagnosed type 1 diabetes. In one embodiment the treatment is started within 12 weeks of diagnosis. In one embodiment the treatment is started within 8 weeks of diagnosis. In one embodiment the treatment is started within 4 weeks of diagnosis.

In one embodiment the GLP-1 agonist, such as a GLP-1 peptide, and the inhibitor of IL-21 function are administered to a subject at risk of developing type 1 diabetes, such as subjects with islet autoantibodies or subjects genetically at-risk without islet autoantibodies.

In one embodiment the invention relates to administration of an effective amount of a GLP-1 agonist, such as a GLP-1 peptide, and an effective amount of an inhibitor of IL-21 function.

Inhibitor of IL-21 Function

According to the invention an inhibitor of IL-21 function is an agent with the ability to inhibit IL-21 mediated signalling and biological effects, such agents may be described as being IL-21 neutralizing. Inhibitors of IL-21 function (also be termed IL-21/IL-21Rα antagonists) for use in the invention are agents with the ability to inhibit IL-21 mediated signalling and biological effects. In a preferred embodiment the IL-21Rα antagonists for use in the present invention are neutralizing anti-IL-21 antibodies having the ability to compete with either γC or the IL-21Rα for binding to IL-21.

In one embodiment the inhibitor of IL-21 function is an antibody that is capable of specifically binding IL-21. In one embodiment the inhibitor of IL-21 function is an anti-IL-21 antibody. In one embodiment the inhibitor of IL-21 function competes with a receptor chain for binding to IL-21, wherein said receptor chain is selected from the list consisting of: IL-21Rα (private chain) and γC (common gamma chain).

In one embodiment the inhibitor of IL-21 function competes with IL-21Rα for binding to IL-21. In one embodiment the inhibitor of IL-21 function binds to helix 1 and 3 of human IL-21.

In one embodiment the inhibitor of IL-21 function binds to a discontinuous epitope on IL-21, wherein said epitope comprises amino acids I37 to Y52 and N92 to P108 as set forth in SEQ ID NO 1.

In one embodiment the inhibitor of IL-21 function binds to a discontinuous epitope on IL-21, wherein said epitope comprises amino acids within the region from I37 to Y52 and within the region N92 to P108 as set forth in SEQ ID NO 1.

In one embodiment the inhibitor of IL-21 function binds to at least one of R34, R38, Q41 and one of K102 and R105 of IL-21 as defined by SEQ ID No 1.

In one embodiment the inhibitor of IL-21 function binds to at least one, at least two, at least 3, at least four or all five of R34, R38, Q41, K012 and R105 of IL-21 as defined by SEQ ID No 1.

In one embodiment the inhibitor of IL-21 function binds to a discontinuous epitope on IL-21, wherein said inhibitor has direct contact (cut off of 4.0 Å) to at least 15 of the amino acids residues 34, 37, 38, 41, 44, 45, 47, 48, 51, 52, 92, 94, 95, 97, 98, 99, 101, 102, 105, 106, 107 and 108.

In one embodiment the antibody has direct contact to I37, R38, Q41, D44, I45, D47, Q48, N51 and Y52 (helix 1 area). In one embodiment the antibody has direct contact to N92, R94, I95, N97, V98, S99, K101, K102, R105, K106, P107 and P108 of (helix 3 area).

An example of an anti-IL-21 antibody competing with IL-21Rα for binding to IL-21 is the "mAb 5" antibody which is a human antibody first disclosed in WO2010055366 as clone number 362.78.1.44. The amino acid sequences of mAb 5 heavy and light chains are shown in SEQ ID NOs 2+3 (IgG1 isotype version). In one embodiment the inhibitor of IL-21 function is mAb 5. The mAb 5 antibody binds to helix 1+3 of human IL-21, or more specifically amino acids I37 to Y52 and N92 to P108, as set forth in SEQ ID NO 1. The binding properties of mAb 5, and variants thereof, and their advantages (high affinity and potency), is described in greater detail in WO2012098113.

In one embodiment the inhibitor of IL-21 function is as described in WO2010/055366 or WO2012098113. In one embodiment the inhibitor of IL-21 function is selected from the group of antibodies listed in Table 1 of WO2010/055366. In one embodiment the inhibitor of IL-21 function is an antibody or antibody fragment produced by the hybridoma designated 362.78.1.44 in WO2010/055366, wherein the hybridoma is deposited with the American Type Culture Collection having the ATCC Patent Deposit Designation PTA-8790.

JBC, VOL. 287, NO. 12, pp. 9454-9460, Mar. 16, 2012 discloses further details about IL-21/IL-21Rα binding.

In one embodiment the inhibitor of IL-21 function is an anti-human IL-21 monoclonal antibody or antibody fragment comprising:
(a) a heavy chain region comprising:
(i) a heavy chain variable region CDR1 comprising SEQ ID NO: 15;

(ii) a heavy chain variable region CDR2 comprising SEQ ID NO: 16; and
(iii) a heavy chain variable region CDR3 comprising SEQ ID NO: 17; and
(b) a light chain region comprising:
(i) a light chain variable region CDR1 comprising SEQ ID NO: 19;
(ii) a light chain variable region CDR2 comprising SEQ ID NO: 20; and
(iii) a light chain variable region CDR3 comprising SEQ ID NO:21 or 22;
and wherein the Fc portion of the antibody is optionally modified with amino acid substitutions to reduce effector function.

In one embodiment the inhibitor of IL-21 function is an anti-human IL-21 monoclonal antibody or antibody fragment comprising i) amino acids residues 20 to 145 of SEQ ID NO: 14 and amino acid residues 21 to 126 of SEQ ID NO: 18; or ii) amino acid residues 1 to 145 of SEQ ID NO: 14 and amino acid residues 1 to 126 of SEQ ID NO: 18; and wherein the Fc portion of the antibody is selected from the group consisting of IgG1, IgG2, IgG3 and IgG4.

The Fc portion may be further optimized for to increase biophysical/biochemical profile or effector function profile.

In one embodiment the inhibitor of IL-21 function comprises the three CDR sequences as set forth in SEQ ID NO 2 and the three CDR sequences as set forth in SEQ ID NO 3.

In one embodiment the inhibitor of IL-21 function is an anti-IL-21 antibody that competes with γC for binding to IL-21. In one embodiment the inhibitor of IL-21 function binds to helix 2 and 4 of human IL-21. In one embodiment the inhibitor of IL-21 function binds to an epitope comprising amino acids Glu 65, Asp 66, Val 67, Glu 68, Thr 69, Asn 70, Glu 72, Trp 73, Lys 117, His 118, Arg 119, Leu 143, Lys 146, Met 147, His 149, Gln 150, and His 151 as set forth in SEQ ID NO 1.

An example of an anti-IL-21 antibody competing with γC for binding to IL-21 is the "mAb 14" antibody which is a human antibody first disclosed in WO2010055366 as done number 366.328.10.63. mAb 14 binds to helix 2+4 of human IL-21. More specifically, mAb 14 binds to Glu 65, Asp 66, Val 67, Glu 68, Thr 69, Asn 70, Glu 72, Trp 73, Lys 117, His 118, Arg 119, Leu 143, Lys 146, Met 147, His 149, Gln 150, and His 151 of human IL-21 as described in WO2012164021. The amino acid sequences of mAb 14 heavy and light chains are shown in SEQ ID NOs 4+5. Further examples of anti-Il-21 antibodies competing with γC for binding to IL-21 are described in WO2012164021

In one embodiment the inhibitor of IL-21 function is mAb 14.

In one embodiment the inhibitor of IL-21 function comprises the three CDR sequences as set forth in SEQ ID NO 4 and the three CDR sequences as set forth in SEQ ID NO 5.

mAb 5 and mAb 14 types of antibodies are generally characterized by having an unusually high affinity (in the nanomolar range) to IL-21 and high potency to neutralize IL-21 induced effects.

In one embodiment the inhibitor of IL-21 function competes with mAb5 for binding to IL-21. The inhibitor may be an antibody of the same bin as mAb5.

In one embodiment the inhibitor of IL-21 function competes with mAb14 for binding to IL-21. The inhibitor may be an antibody of the same bin as mAb5.

Further embodiments of inhibitors of IL-21 function or neutralizing IL-21Rα antagonists for use in the invention are those that compete with IL-21 for binding to IL-21Rα. IL-21Rα antagonists for use in the invention are preferably agents binding the loops connecting the β-strands of IL-21Rα. The AB, CD, EF, B'C', and F"G' loops and the linker all contain residues involved in binding IL-21. In IL-21R, Tyr 36 in the CD loop, Met 89 and Asp 91 in the EF loop, and Tyr 148 in the B'C' loop contribute the most to the binding surface. The most important loop is the EF loop, which supplies 7 of the 20 amino acids of IL-21R that are involved in binding IL-21.

Anti IL-21R antibodies for use in the invention may bind to the EF loop. Preferred anti-IL-21R antibodies for use in the invention binds to a group of at least 10 amino acid residues selected from: Tyr 29, Gln 52, Gln 54, Tyr 55, Glu 57, Leu 58, Phe 86, His 87, Phe 88, Met 89, Ala 90, Asp 91, Asp 92, Ile 93, Leu 113, Ala 115, Pro 145, Ala 146, Tyr 148, Met 149, Lys 153, Ser 209, Tyr 210 of IL-21R (SEQ ID NO 6).

IL-21/IL-21Rα such as anti-IL-21R antibodies or antagonists for use in the invention are antibodies that interfere with binding of IL-21Rα with γC and thus assembly of the IL-21/IL-21Rα/γC complex.

In one embodiment the inhibitor of IL-21 function binds IL-21 and thereby inhibits IL-21 function. The inhibitor of IL-21 function may be a fusion protein comprising a fragment of the IL-21 receptor which binds IL-21, such as the recombinant product "IL-21R(human):Fc(human) (rec.)" produced by Chimerigen and commercially available from, for example, www.biomol.de as item no. CHI-HF-21021R-C100.

In one embodiment the inhibitor of IL-21 function specifically binds to IL-21 with a binding affinity of $10^7$ $M^{-1}$ or greater, $10^8$ $M^{-1}$ or greater, $10^9$ $M^{-1}$ or greater, $10^{10}$ $M^{-1}$ or greater, $10^{10}$ $M^{-1}$ or greater, or $10^{12}$ $M^{-1}$ or greater.

A "neutralizing" IL-21 inhibitor or antibody according to the invention is a molecule having the ability to significantly inhibit signalling through the IL-21Rα. Neutralizing effects can be assessed in various functional assays using cells expressing IL-21R and γC, e.g. such as the bioactivity assay using NK92 cells and B cell proliferation assays as disclosed in WO2012/098113 and WO2012/164021 and exemplified in Assay III and IV herein. An $IC_{50}$ in the nanomolar range in B-cell proliferation assay is considered a highly effective neutralizing IL-21 inhibitor. In general molecules with neutralizing effects similar to the antibodies described herein are to be considered neutralizing inhibitors of IL-21.

The term "antibody", "recombinant antibody", "monoclonal antibody" and "mAb" as used herein, is intended to refer to immunoglobulin molecules and fragments thereof according to the invention that have the ability to specifically bind to an antigen. Full-length antibodies comprise four (or more) polypeptide chains, i.e. at least two heavy (H) chains and at least two light (L) chains interconnected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hyper-variability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Variable regions and CDRs in an antibody sequence may be identified by aligning the sequences against a database of known variable regions (frameworks and CDRs are defined according to the Kabat numbering scheme herein—(Kabat, E A, Wu, T T, Perry, H M, et al. Sequences of Proteins of Immunological Interest, Fifth Edition. US Department of Health and Human Services, Public Health Service, National Institutes of Health, NIH Publication No. 91-3242, 1991).

The fragment crystallizable region ("Fc region"/"Fc domain") of an antibody comprises the tail regions of an antibody that interact with cell surface receptors called Fc receptors and some proteins of the complement system. This property allows antibodies to activate the immune system. The Fc domain can, however, comprise amino acid mutations that result in modification of these effector functions. Preferably, a modified Fc domain comprises one or more, preferably all of the following mutations that will result in decreased affinity to certain Fc receptors (L234A, L235E, and G237A) and in reduced C1q-mediated complement fixation (A330S and P331S), respectively (residue numbering according to the EU index). Such Fc domains will still retain a long in vivo circulatory half-life.

The other part of an antibody, called the "Fab region"/ "Fab domain"/"Fab fragment", contains variable regions that define the specific target that the antibody can bind. Fab fragments can be produced from intact antibodies using well known methods, for example by proteolytic cleavage with enzymes such as papain (to produce Fab fragments) or pepsin (to produce F(ab')2 fragments). Alternatively, antibody fragments may be produced recombinantly, using standard recombinant DNA and protein expression technologies.

Examples of binding fragments encompassed within the term "antibody" thus include but are not limited to: (i) a Fab fragment, a monovalent fragment consisting of the VL, VH, CL and CH1 domains; (ii) F(ab)2 and F(ab')2 fragments, a bivalent fragment comprising two Fab fragments linked by a disulfide bridge at the hinge region; (iii) a Fd fragment consisting of the VH and CH1 domains; (iv) a scFv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Such single chain antibodies are also intended to be encompassed within the term "antibody". Other forms of single chain antibodies, such as diabodies are also encompassed within the term "antibody". Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Hol-liger, P., et al. (1993) Proc. Natl. Acad. Sci. USA 90:6444-6448; Poljak, R. J., et al. (1994) Structure 2:1121-1123).

It is understood that the antigen may have one or more epitopes comprising (1) antigenic determinants which consist of single peptide chains, (2) conformational epitopes comprising one or more spatially contiguous peptide chains whose respective amino acid sequences are located disjointedly along polypeptide sequence; and (3) post-translational epitopes which comprise, either in whole or part, molecular structures covalently attached to the antigen after translation, such as carbohydrate groups, or the like.

The terms "human antibody", "human antibodies", as used herein, means antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

Antibodies in which CDR sequences derived from antibodies originating from another mammalian species (such as e.g. a mouse), have been grafted onto human framework sequences and optionally potentially further engineered by mutagenesis are referred to as "humanized antibodies".

The term "chimeric antibody" or "chimeric antibodies" refers to antibodies according to the invention where the light and heavy chain genes have been constructed, typically by genetic engineering, from immunoglobulin variable and constant region genes belonging to different species. For example, the variable segments of genes from a mouse monoclonal antibody may be joined to human constant segments.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined through various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immuno-dominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

The term "affinity", as used herein, defines the strength of the binding of an receptor and a ligand, frequently the binding of an antibody to an epitope. The affinity of an antibody is measured by the equilibrium dissociation constant KD, defined as [Ab]×[Ag]/[Ab–Ag] where [Ab–Ag] is the molar concentration of the antibody-antigen complex, [Ab] is the molar concentration of the unbound antibody and [Ag] is the molar concentration of the unbound antigen at equilibrium. KD can also be described from the kinetics of complex formation and dissociation, determined by e.g. the SPR method. The rate constants corresponding to the association and the dissociation of a monovalent complex are referred to as the association rate constant ka (or kon) and dissociation rate constant kd (or koff), respectively. KD is then related to ka and kd through the equation KD=kd/ka. The affinity constant KA is defined by 1/KD. Preferred methods for determining antibody specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983). Use of high affinity antibodies are preferred in connection with the present invention, e.g. antibodies binding specifically to the antigen with a binding affinity as measured by e.g. SPR of e.g. 107 M–1 or greater, 108 M–1 or greater, 109 M–1 or greater, 1010 M–1 or greater, 1011 M–1 or greater, or 1012 M–1 or greater.

In one embodiment the terms "anti-IL-21 antibody" and "anti-IL-21" are used interchangeably herein and refer to an antibody which has the ability to specifically bind to IL-21.

IL-21/IL-21Rα antagonists, such as anti-IL-21 antibodies, for use in the invention may be produced by means of recombinant nucleic acid techniques. In general, a cloned wild-type Protein X nucleic acid sequence is modified to encode the desired protein. This modified sequence is then inserted into an expression vector, which is in turn transformed or transfected into host cells.

Sequences

For further sequence information reference to the sequence listing is made.

```
SEQ ID No 1: hIL-21 (incl. signal peptide spanning amino acids 1-29-mAb 5
epitope shown in bold; IL-21Ra binding site shown in underline; amino acid residues
forming the mAb 14 epitope shown with lower case letters in italics).
MRSSPGNMERIVICLMVIFLGTLVHKSSSQGQDRHMIRMRQLIDIVDQLKNYVNDLVP
EFLPAPedvetnCewSAFSCFQKAQLKSANTGNNERIINVSIKKLKRKPPSTNAGRRQkhrLTCPSC
DSYEKKPPKEFLERFKS/LQkmIhqhLSSRTHGSEDS.

The four helix' spanning the following amino acids; Helix 1 aa 32-57, Helix 2 aa
72-81, Helix 3 aa 93-103 and Helix 4 aa 133-149.

SEQ ID No 2: "mAb 5": light chain (signal peptide omitted-CDR sequences
shown in bold/underline-constant region shown in lowercase letters):
EIVLTQSPGTLSLSPGERATLSCRASQSVSSSYLAWYQQKPGQAPRLLIYGASSRATGIP
DRFSGSGSGTDFTLTISRLEPEDFAVYYCQQYGSWTFGQGTKVEIKRtvaapsvfifppsdeqlksgtasv
vcllnnfypreakvqwkvdnalqsgnsqesvteqdskdstyslsstltlskadyekhkvyacevthqglsspvtksfnrgec.

SEQ ID No 3: "mAb 5": heavy chain of the IgG1 isotype (signal peptide omitted
CDR sequences shown in bold/underline-constant region shown in lowercase letters):
QVQLVESGGGVVQPGRSLRLSCAASGFTFSSYGMHWVRQAPGKGLEWVAFIWYDGSD

KYYADSVKGRFTISRDNSKNTLYLQMNSLRAEDTAVYYCARDGDSSDWYGDYYFGMDVWGQG

TTVTVSSastkgpsvfplapsskstsggtaalgclvkdyfpepvtvswnsgaltsgvhtfpavlqssglyslssvvtvpssslg tqtyicnvnhkpsntkvdkkvepkscdkthtcppcpapeaegapsvflfppkpkdtlmisrtpevtcvvvdvshedpevkf nwyvdgvevhnaktkpreeqynstyrvvsvltvlhqdwIngkeykckvsnkalpssiektiskakgqprepqvytlppsrd eltknqvsltclvkgfypsdiavewesngqpennykttppvldsdgsfflyskltvdksrwqqgnvfscsvmhealhnhytqk slslspgk.

SEQ ID No 4: "mAb 14" light chain (signal peptide omitted-CDR sequences
shown in bold/underline, constant region shown in lowercase letters):
AIQLTQSPSSLSASVGDRVTITCRASQDIDSALAWYQQKPGKAPKILIHDASSLESGVP
SRFSGSGSGTDFTLTISSLQPEDFATYYCQQFNSYPYTFGQGTKLEIKRtvaapsvfifppsdeqlksgtas
vvcllnnfypreakvqwkvdnalqsgnsqesvteqdskdstyslsstltlskadyekhkvyacevthqglsspvtksfnrgec.

SEQ ID No 5: "mAb 14" heavy chain of the IgG4 isotype (signal peptide omitted
CDR sequences shown in bold/underline, constant region shown in lowercase letters):
EVQLVESGGGLVKPGGSLRLSCAASGFIFSSYSMNWVRQAPGKGLEWVSSITSGSYYI HYADSVKGRFTISRDNAKNSLYLQMNSLRAEDTAVYYCVRERGWGYYGMDVWGQGTTVTVSSa stkgpsvfplapcsrstsestaalgclvkdyfpepvtvswnsgaltsgvhtfpavlqssglyslssvvtvpssslgtktytcnvdh
```

-continued kpsntkvdkrveskygppcpscpapeflggpsvflfppkpkdtlmisrtpevtcvvvdvsqedpevqfnwyvdgvevhna ktkpreeqfnstyrvvsvltvlhqdwlngkeykckvsnkglpssiektiskakgqprepqvytlppsqeemtknqvsltclvk gfypsdiavewesngqpennykttppvldsdgsfflysrltvdksrwqegnvfscsvmhealhnhytqkslslslgk.

SEQ ID No 6: IL-21Ra (incl. signal sequence):
MPRGWAAPLLLLLLQGGWGCPDLVCYTDYLQTVICILEMWNLHPSTLTLTWQDQYEELKD

EATSCSLHRSAHNATHATYTCHMDVFHFMADDIFSVNITDQSGNYSQECGSFLLAESIKPAPPFNVT

VTFSGQYNISWRSDYEDPAFYMLKGKLQYELQYRNRGDPWAVSPRRKLISVDSRSVSLLPLEFRKDS

SYELQVRAGPMPGSSYQGTWSEWSDPVIFQTQSEELKEGWNPHLLLLLLLVIVFIPAFWSLKTHPLW

RLWKKIWAVPSPERFFMPLYKGCSGDFKKWVGAPFTGSSLELGPWSPEVPSTLEVYSCHPPRSPAKR

LQLTELQEPAELVESDGVPKPSFWPTAQNSGGSAYSEERDRPYGLVSIDTVTVLDAEGPCTWPCSCE

DDGYPALDLDAGLEPSPGLEDPLLDAGTTVLSCGCVSAGSPGLGGPLGSLLDRLKPPLADGEDWAG

GLPWGGRSPGGVSESEAGSPLAGLDMDTFDSGFVGSDCSSPVECDFTSPGDEGPPRSYLRQWVVI

PPPLSSPGPQAS.

SEQ ID No 7: γC (Common gamma chain/IL-2Rγ) incl. signal sequence:
MLKPSLPFTSLLFLQLPLLGVGLNTTILTPNGNEDTTADFFLTTMPTDSLSVSTLPLPEVQCFV

FNVEYMNCTWNSSSEPQPTNLTLHYWYKNSDNDKVQKCSHYLFSEEITSGCQLQKKEIHLYQTFVV

QLQDPREPRRQATQMLKLQNLVIPWAPENLTLHKLSESQLELNWNNRFLNHCLEHLVQYRTDWDHS

WTEQSVDYRHKFSLPSVDGQKRYTFRVRSRFNPLCGSAQHWSEWSHPIHWGSNTSKENPFLFALE

AVVISVGSMGLIISLLCVYFWLERTMPRIPTLKNLEDLVTEYHGNFSAWSGVSKGLAESLQPDYSERL

CLVSEIPPKGGALGEGPGASPCNQHSPYWAPPCYTLKPET.

SEQ ID No 11: Recombinant mouse IL-21:
MHKSSPQGPD RLLIRLRHLI DIVEQLKIYE NDLDPELLSA PQDVKGHCEH
AAFACFQKAK LKPSNPGNNK TFIIDLVAQL RRRLPARRGG KKQKHIAKCP SCDSYEKRTP
KEFLERLKWL LQKMIHQHLS SEQ ID No 12: amino acid sequence of mouse surrogate anti-IL-21 variable
light chain (mIgG1/kappa isotype)
MDFQVQIFSF LLISASVILS RGQTVLIQSP AIMSASPGEK VTMTCSASSS
VSYMHWYQQK SGTSPKRWIY DTSKLASGVP ARFSGSGSGT SYSLTISSME AEDAATYYCQ
QWNSNPPTFG GGTKLEMK SEQ ID No 13: amino acid sequence of mouse surrogate anti-IL-21-variable
heavy chain (mIgG1/kappa isotype):
MNFGPSLIFL VLILKGVQCE VQLVESGGGL VKPGGSLKLS CAASGFTFNR
YSMSWVRQSP EKRLEWVAEI SVGGSYTQYV DIVTGRFTIS RDNAKNTLYL EMSSLRSEDT
AMYYCARLYY SGSGDSYYYA MDYWGQGTSV TVSS SEQ ID No 14:
MEFGLSWVFL VALLRGVQCQ VQLVESGGGV VQPGRSLRLS CAASGFTFSS
YGMHWVRQAP GKGLEWVAFI WYDGSDKYYA DSVKGRFTIS RDNSKNTLYL QMNSLRAEDT
AVYYCARDGD SSDWYGDYYF GMDVWGQGTT VTVSS SEQ ID No 15:
SYGMH SEQ ID No 16:
FIWYDGSDKY YADSVKG SEQ ID No 17:
DGDSSDWYGD YYFGMDV SEQ ID No 18:
METPAQLLFL LLLWLPDTTG EIVLTQSPGT LSLSPGERAT
LSCRASQSVS SSYLAWYQQK PGQAPRLLIY GASSRATGIP DRFSGSGSGT DFTLTISRLE
PEDFAVYYCQ QYGSWTFGQG TKVEIK SEQ ID No 19:
RASQSVSSSY LA SEQ ID No 20:
GASSRAT SEQ ID No 21:
QQYGSWT SEQ ID No 22:
TYGMH GLP-1 Receptor Agonists A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" or a "GLP-1 agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to human GLP-1.

GLP-1 Agonists

In one embodiment the GLP-1 agonist is a GLP-1 peptide selected from GLP-1 (7-35), GLP-1 (7-36), GLP-1 (7-36)-amide, GLP-1 (7-37), GLP-1 (7-38), GLP-1 (7-39), GLP-1 (7-40), GLP-1 (7-41) or an analogue or derivative thereof. In one embodiment the GLP-1 peptide comprises no more than 15, such as no more than 10 or no more than 6, amino acid residues which have been substituted, inserted or deleted as compared to GLP-1 (7-37). In one embodiment the GLP-1 peptide comprises no more than 5, such as no more than 4 or no more than 3, amino acid residues which have been substituted, inserted or deleted as compared to GLP-1 (7-37). In one embodiment the GLP-1 peptide comprises no more than 4 amino acid residues which are not encoded by the genetic code.

In yet another embodiment, the GLP-1 agonist is exendin-4 or exendin-3, an exendin-4 or exendin-3 analogue, or a derivative of any of these.

In one embodiment the GLP-1 agonists for use in the invention have GLP-1 activity. In one embodiment a "GLP-1 agonist" is understood to refer to any compound, including peptides and non-peptide compounds, which fully or partially activate the human GLP-1 receptor. In one embodiment the "GLP-1 agonist" is any peptide or non-peptide small molecule that binds to a GLP-1 receptor, preferably with an affinity constant ($K_D$) or a potency ($EC_{50}$) of below 1 µM, e. g. below 100 nM as measured by methods known in the art (see e. g., WO 98/08871).

In one embodiment a "GLP-1 agonist" is understood to refer to a peptide, which fully or partially activates the human GLP-1 receptor. In one embodiment the "GLP-1 agonist" is any peptide that binds to a GLP-1 receptor, preferably with an affinity constant ($K_D$) or a potency ($EC_{50}$) of below 1 µM, e. g. below 100 nM as measured by methods known in the art (see e. g., WO 98/08871). In one embodiment "a GLP-1 agonist" is understood to refer to any compound, including peptides and non-peptide compounds, which fully or partially activate the human GLP-1 receptor. In one embodiment the "GLP-1 peptide" is any peptide or non-peptide small molecule that binds to a GLP-1 receptor, preferably with an affinity constant ($K_D$) or a potency ($EC_{50}$) of below 1 µM, e. g. below 100 nM as measured by methods known in the art (see e. g., WO 98/08871). In one embodiment a "GLP-1 agonist" is not a non-peptide compound, such as a non-peptide small molecule.

In one embodiment methods for identifying GLP-1 agonists are described in WO 93/19175 (Novo Nordisk A/S) and examples of suitable GLP-1 agonists which can be used according to the present invention includes those referred to in WO 2005/027978 (Novo Nordisk A/S), the teachings of which are both incorporated by reference herein. "GLP-1 activity" refers to the ability to bind to the GLP-1 receptor and initiate a signal transduction pathway resulting in insulinotropic action or other physiological effects as is known in the art. For example, the GLP-1 agonists of the invention can be tested for GLP-1 activity using the assay described in Assay (I) herein. In one embodiment the GLP-1 agonist has an EC50 at or below 3000 pM, such as at or below 500 pM or at or below 100 pM, optionally determined by Assay (I).

In yet another embodiment the GLP-1 agonist is a stable GLP-1 agonist As used herein "a stable GLP-1 agonist" (e.g. a "stable GLP-1 peptide") means a GLP-1 agonist which exhibits an in vivo plasma elimination half-life of at least 24 hours in man, optionally determined by the method described below. Examples of stable GLP-1 agonists (e.g. GLP-1 peptides) can be found in WO2006/097537. In one embodiment the GLP-1 agonist is a DPPIV protected GLP-1 peptide. In one embodiment the GLP-1 peptide is DPPIV stabilised.

In one embodiment the GLP-1 agonist has a half-life of at least 24 hours, such as at least 48 hours, at least 60 hours, or at least 72 hours, or such as at least 84 hours, at least 96 hours, or at least 108 hours, or optionally at least 120 hours, at least 132 hours, or at least 144 hours, wherein said half-life optionally is determined in humans or minipigs, e.g. by Assay (II).

In one embodiment the method for determination of plasma elimination half-life of a compound in man may be carried out as follows: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e. g., Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43 (51), 2000. Derived pharmacokinetic parameters are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

In one embodiment the GLP-1 agonist is a GLP-1 derivative. In one such embodiment the GLP-1 peptide is attached to a hydrophilic spacer via the amino acid residue in position 23, 26, 34, 36 or 38 relative to the amino acid sequence of GLP-1 (7-37).

In one embodiment the GLP-1 derivative comprises an albumin binding residue which is covalently attached, optionally via a hydrophilic spacer. In one embodiment said albumin binding residue is covalently attached, optionally via a hydrophilic spacer, to the C-terminal amino acid residue of said GLP-1 peptide or an amino acid residue which is not the C-terminal amino acid residue. In one embodiment the GLP-1 peptide is attached to a hydrophilic spacer via the amino acid residue in position 23, 26, 34, 36 or 38 relative to the amino acid sequence of GLP-1 (7-37).

Human Glucagon-Like Peptide-1 is GLP-1(7-37) and has the sequence HAEGTFTSDVSSYLEGQAAKEFIAWLVK-GRG (SEQ ID No 8). GLP-1(7-37) may also be designated "native" GLP-1. In the sequence listing, the first amino acid residue of GLP-1(7-37) (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37. GLP-1 analogues may be referenced using the corresponding aa positions.

A non-limiting example of a suitable analogue nomenclature is [Aib$^8$,Arg$^{34}$,Lys$^{37}$]GLP-1(7-37), which designates a GLP-1(7-37) analogue, in which the alanine at position 8 has been substituted with α-aminoisobutyric acid (Aib), the lysine at position 34 has been substituted with arginine, and the glycine at position 37 has been substituted with lysine.

The term "peptide", as e.g. used in the context of the GLP-1 peptides of the invention, refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids. In particular embodiments the peptide consists of, i) 29, ii) 30, iii) 31, or iv) 32 amino acids.

In one embodiment the GLP-1 peptide exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31-1)/31. In one embodiment non-peptide moieties of the GLP-1 peptide are not included when determining sequence identity.

The term "derivative" is herein distinct from the term "conjugate". A derivative, such as a GLP-1 derivative, comprises one or more substituents or side chains of a well-defined structure covalently attached to one or more specific amino acid residues of the peptide, herein mainly a GLP-1 peptide. A conjugate, in turn, refers to a compound having a large, typically recombinant molecule (such as IgG-Fc or albumin) covalently bound to the peptide via a synthetic linker (thereby distinguished from fusion proteins).

In one embodiment the GLP-1 agonist is a GLP-1 peptide derivative. In one embodiment the term "derivative" as used herein in the context of a GLP-1 peptide or analogue means a chemically modified GLP-1 peptide or analogue, in which one or more substituents have been covalently attached to the peptide or analogue. The substituent may also be referred to as a side chain (not to be mixed with amino acid side chains). Typical modifications are amides, carbohydrates, alkyl groups, acyl groups, esters and the like. An example of a derivative of GLP-1(7-37) is $N^{\epsilon 26}$-(γ-Glu($N^\alpha$-hexadecanoyl))-[Arg$^{34}$, Lys$^{25}$]) GLP-1 (7-37). In a particular embodiment, the side chain is capable of forming non-covalent aggregates with albumin, thereby promoting the circulation of the GLP-1 peptide with the blood stream, and also having the effect of protracting the time of action of the GLP-1 peptide, due to the fact that the aggregate of the GLP-1 peptide and albumin is only slowly disintegrated to release the active pharmaceutical ingredient. Thus, the substituent, or side chain, as a whole may be referred to as an albumin binding moiety.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion in between the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by acylation. Additional or alternative means for preparing a derivative includes alkylation, ester formation, or amide formation, or coupling to a cysteine residue, such as by maleimide or haloacetamide (such as bromo-/fluoro-/iodo-) coupling.

In one embodiment an active ester of the albumin binding moiety, e.g. comprising a protracting moiety and a linker, is covalently linked to an amino group of a lysine residue, e.g. the epsilon amino group thereof, under formation of an amide bond (this process being referred to as acylation).

Unless otherwise stated, when reference is made to an acylation of a lysine residue, it is understood to be to the epsilon-amino group thereof.

For the present purposes, the terms "albumin binding moiety", "protracting moiety", and "linker" may include the unreacted as well as the reacted forms of these molecules. Whether or not one or the other form is meant is clear from the context in which the term is used.

Usually, the protracting moiety is connected to an epsilon amino group of Lys at the specified position via a linker, and likewise in one embodiment all connections between protracting moiety, linker and peptide are amide bonds.

Due to the half-life extending properties fatty acids may be used as said albumin binding residues and in particular as a key part of the protracting moieties. For the attachment to the GLP-1 peptide, the acid group of the fatty acid, or one of the acid groups of the fatty diacid is attached via an amide bond with the epsilon amino group of a lysine residue in the GLP-1 peptide either directly or through a linker.

In one embodiment the GLP-1 derivative is mono acylated. In an embodiment the GLP-1 derivative is acylated at K26.

In one embodiment the GLP-1 derivative is di-acylated. In an embodiment the GLP-1 derivative is acylated at K26 and K37, K27 and K36 or K38 and K42.

In one embodiment the term "fatty acid" refers to aliphatic monocarboxylic acids having from 4 to 28 carbon atoms, it is optionally unbranched, and/or even numbered, and it may be saturated or unsaturated.

In one embodiment the term "fatty diacid" refers to fatty acids as defined above but with an additional carboxylic acid group in the omega position. Thus, fatty diacids are dicarboxylic acids.

In one embodiment the protracting moiety or moieties comprise(s) one or more fatty acids selected independently from C14-C20 fatty acids and C16-C20 fatty diacids.

In an embodiment a protracting moiety may comprise a C16 fatty acid ($CH_3$—$(CH_2)_{14}$—CO—).

In an embodiment a protracting moiety may comprise C18 diacid radical (HOOC—$(CH_2)_{16}$—CO—). In an embodiment a protracting moiety may comprise C20 diacid radical (HOOC—$(CH_2)_{18}$—CO—).

In one embodiment a protracting moiety may comprise a 4-COOH-PhO— fatty acid, where the 4-COOH-PhO— structure is followed by —$(CH2)_y$—C(=O)- where y is 7-11.

In one embodiment a protracting moiety may comprise Chem 9, wherein y=9.

Chem. 4

In one embodiment one or more or the protracting moiety of the GLP-1 peptide derivative is/are attached via a linker.

The linker(s) of the GLP-1 derivative of the invention may in an embodiment comprise the following first linker element:

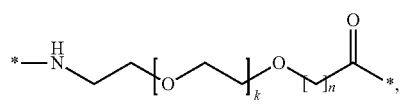

Chem. 5 wherein k is an integer in the range of 1-5, and n is an integer in the range of 1-5.

In a particular embodiment, when k=1 and n=1, this linker element may be designated OEG, or a di-radical of 8-amino-3,6-dioxaoctanic acid, and/or it may be represented by the following formula:

*—NH—$(CH_2)_2$—O—$(CH_2)_2$—O—$CH_2$—CO—*.  Chem. 5a:

In another particular embodiment, each linker of the GLP-1 peptide of the invention may further comprise, independently, a second linker element, e.g. a Glu di-radical, such as Chem. 6 and/or Chem. 7:

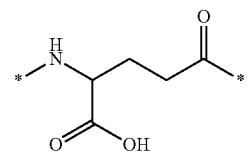

Chem. 6

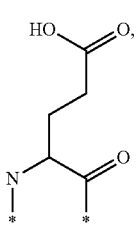

Chem. 7 wherein the Glu di-radical may be included p times, where p is an integer in the range of 1-3.

Chem. 6 may also be referred to as gamma-Glu, or briefly gGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem. 7 may also be referred to as alpha-Glu, or briefly aGlu, or simply Glu, due to the fact that it is the alpha carboxy group of the amino acid glutamic acid which is here used for connection to another linker element, or to the epsilon-amino group of lysine.

The above structures of Chem. 6 and Chem. 7 cover the L-form, as well as the D-form of Glu. In particular embodiments, Chem. 6 and/or Chem. 7 is/are, independently, a) in the L-form, or b) in the D-form.

In still further particular embodiments the linker has a) from 5 to 41 C-atoms; and/or b) from 4 to 28 hetero atoms.

The concentration in plasma of the GLP-1 agonists (e.g. GLP-1 peptides) of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI (Luminescent Oxygen Channeling Immunoassay), generally as described for the determination of insulin by Poulsen and Jensen in Journal of Biomolecular Screening 2007, vol. 12, p. 240-247—briefly blood samples may be collected at desired intervals, plasma separated, immediately frozen, and kept at −20° C. until analyzed for plasma concentration of the respective GLP-1 agonist (e.g. GLP-1 peptide); the donor beads are coated with streptavidin, while acceptor beads are conjugated with a monoclonal antibody recognising a mid-/C-terminal epitope of the peptide;

another monoclonal antibody, specific for the N-terminus, is biotinylated; the three reactants are combined with the analyte and formed a two-sited immuno-complex; illumination of the complex releases singlet oxygen atoms from the donor beads, which are channeled into the acceptor beads and triggered chemiluminescence which may be measured in an Envision plate reader; the amount of light is proportional to the concentration of the compound.

In one embodiment the GLP-1 agonist, such as the GLP-1 peptide, comprises the amino acid sequence of the formula (I) (SEQ ID NO 9):

$$Xaa_7\text{-}Xaa_8\text{-}Glu\text{-}Gly\text{-}Thr\text{-}Phe\text{-}Thr\text{-}Ser\text{-}Asp\text{-}Xaa_{16}\text{-}Ser\text{-}Xaa_{18}\text{-}Xaa_{19}Xaa_{20}GluXaa_{22}\text{-}Xaa_{23}\text{-}Ala\text{-}Xaa_{25}\text{-}Xaa_{26}\text{-}Xaa_{27}\text{-}Phe\text{-}Ile\text{-}Xaa_{30}\text{-}Trp\text{-}Leu\text{-}Xaa_{33}\text{-}Xaa_{34}\text{-}Xaa_{35}\text{-}Xaa_{36}\text{-}Xaa_{37}\text{-}Xaa_{38}\text{-}Xaa_{39}\text{-}Xaa_{40}\text{-}Xaa_{41}\text{-}Xaa_{42}\text{-}Xaa_{43}\text{-}Xaa_{44}\text{-}Xaa_{45}\text{-}Xaa_{46} \quad \text{Formula (I):}$$

wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocydobutyl) carboxylic acid, (1-aminocydopentyl) carboxylic acid, (1-aminocyclohexyl) carboxylic acid, (1-aminocydoheptyl) carboxylic acid, or (1-aminocydooctyl) carboxylic acid;

$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly, Glu or Aib;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val or Lys;
$Xaa_{34}$ is Lys, Glu, Asn or Arg;
$Xaa_{35}$ is Gly or Aib;
$Xaa_{36}$ is Arg, Gly or Lys;
$Xaa_{37}$ is Gly, Ala, Glu, Pro, Lys, amide or is absent;
$Xaa_{38}$ is Lys, Ser, amide or is absent;
$Xaa_{39}$ is Ser, Lys, amide or is absent;
$Xaa_{40}$ is Gly, amide or is absent;
$Xaa_{41}$ is Ala, amide or is absent;
$Xaa_{42}$ is Pro, amide or is absent;
$Xaa_{43}$ is Pro, amide or is absent;
$Xaa_{44}$ is Pro, amide or is absent;
$Xaa_{45}$ is Ser, amide or is absent;
$Xaa_{46}$ is amide or is absent;

provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

In one embodiment the GLP-1 agonist, such as the GLP-1 peptide, comprises the amino acid sequence of formula (II) (SEQ ID NO 10):

$$Xaa_7\text{-}Xaa_8\text{-}Glu\text{-}Gly\text{-}Thr\text{-}Phe\text{-}Thr\text{-}Ser\text{-}Asp\text{-}Val\text{-}Ser\text{-}Xaa_{18}\text{-}Tyr\text{-}Leu\text{-}Glu\text{-}Xaa22\text{-}Xaa_{23}\text{-}Ala\text{-}Ala\text{-}Xaa_{26}\text{-}Glu\text{-}Phe\text{-}Ile\text{-}Xaa_{30}\text{-}Trp\text{-}Leu\text{-}Val\text{-}Xaa_{34}\text{-}Xaa_{35}\text{-}Xaa_{36}\text{-}Xaa_{37}Xaa_{38} \quad \text{Formula (II):}$$

wherein $Xaa_7$ is L-histidine, D-histidine, desamino-histidine, 2-amino-histidine, -hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocydobutyl) carboxylic acid, (1-aminocydopentyl) carboxylic acid, (1-aminocyclohexyl) carboxylic acid, (1-aminocydoheptyl) carboxylic acid, or (1-aminocydooctyl) carboxylic acid;

$Xaa_{18}$ is Ser, Lys or Arg;
$Xaa_{22}$ is Gly, Glu or Aib;
$Xaa_{23}$ is Gin, Glu, Lys or Arg;
$Xaa_{26}$ is Lys, Glu or Arg; Xaa30 is Ala, Glu or Arg;
$Xaa_{34}$ is Lys, Glu or Arg;
$Xaa_{35}$ is Gly or Aib;
$Xaa_{36}$ is Arg or Lys;
$Xaa_{37}$ is Gly, Ala, Glu or Lys;
$Xaa_{38}$ is Lys, amide or is absent.

In one embodiment the GLP-1 agonist, such as the GLP-1 peptide, is liraglutide. Liraglutide is a mono-acylated GLP-1 peptide for once daily administration which is marketed by Novo Nordisk A/S, and is disclosed in WO98/08871 Example 37.

In one embodiment the present invention encompasses pharmaceutically acceptable salts of the GLP-1 agonists (e.g. GLP-1 peptides). Such salts include pharmaceutically acceptable acid addition salts, pharmaceutically acceptable metal salts, ammonium, and alkylated ammonium salts. Also intended as pharmaceutically acceptable acid addition salts are the hydrates which the present GLP-1 agonists (e.g. GLP-1 peptides) are able to form.

In one embodiment the GLP-1 peptide comprises an Aib residue in position 8. In one embodiment the term "Aib" as used herein refers to α-aminoisobutyric acid.

In one embodiment the amino acid residue in position 7 of said GLP-1 peptide is selected from the group consisting of D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine and 4-pyridylalanine.

In one embodiment the GLP-1 agonist peptide comprises the amino acid sequence of the following formula: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO:23).

In one embodiment the GLP-1 agonist comprises an albumin binding residue attached via a hydrophilic spacer to the C-terminal amino acid residue of said GLP-1 peptide.

In one embodiment the GLP-1 agonist comprises a second albumin binding residue is attached to an amino acid residue which is not the C-terminal amino acid residue.

In one embodiment the GLP-1 agonist (e.g. GLP-1 peptide) is selected from the group consisting of liraglutide and semaglutide.

Liraglutide is a mono-acylated GLP-1 agonist for once daily administration which is marketed as of 2009 by Novo Nordisk A/S, is disclosed in WO 98/08871 Example 37.

In one embodiment the GLP-1 peptide is semaglutide. WO 06/097537 discloses semaglutide (Example 4), a mono-acylated GLP-1 agonist for once weekly administration. In one embodiment the GLP-1 peptide has the structure His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg (SEQ ID NO:24).

In one embodiment the GLP-1 peptide comprises Arg34GLP-1 (7-37) or [Aib8,Arg34]GLP-1-(7-37).

In one embodiment the GLP-1 agonist comprises an Fc fragment of an IgG. In one embodiment the GLP-1 agonist comprises an Fc fragment of an IgG and one or more, such as two, GLP-1 peptides.

In one embodiment the GLP-1 agonist is selected from albiglutide and dulaglitide.

In one embodiment the GLP-1 peptide has the following structure: His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg (SEQ ID NO:24).

In one embodiment the GLP-1 peptide has the following structure: (SEQ ID NO:25) (His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg)$_2$-recombinantly fused to human albumin.

In one embodiment the GLP-1 agonist is formulated so as to have a half-life in man of at least 48 hours. This may be obtained by sustained release formulations known in the art.

In yet another embodiment, the GLP-1 agonist is exendin-4 or exendin-3, an exendin-4 or exendin-3 analogue, or a derivative of any of these.

In one embodiment the GLP-1 peptide is selected from the group consisting of exenatide, albiglutide, and dulaglitide.

In one embodiment the GLP-1 peptide is exenatide. In one embodiment the GLP-1 peptide comprises the amino acid sequence of the formula: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO:23). Exenatide is a synthetic version of exendin-4, a hormone found in the saliva of the Gila monster. Exenatide displays biological properties similar to GLP-1. In some embodiments the composition is BYDUREON® (a long acting release formula of exenatide in PLGA particles). In one embodiment the "Bydureon® composition" refer to a powder comprising exenatide, poly (D,L-lactide-co-glycolide), and sucrose which immediately prior to injection is reconstituted in a solvent comprising carmellose sodium, sodium chloride, polysorbate 20, monobasic sodium phosphate (e.g. its monohydrate), dibasic sodium phosphate (e.g. its heptahydrate), and water for injections.

In one embodiment the GLP-1 peptide has the structure (SEQ ID NO:25) (His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg)2-genetically fused to human albumin. Albiglutide is a recombinant human serum albumin (HSA)-GLP-1 hybrid protein, likely a GLP-1 dimer fused to HSA. The constituent GLP-1 peptide is analogue, in which Ala at position 8 has been substituted by Glu.

In one embodiment the GLP-1 peptide is dulaglitide. Dulaglutide is a GLP-1-Fc construct (GLP-1-linker-Fc from IgG4).

Pharmaceutical Composition

Preparations of pharmaceutical compositions are known in the art. For convenience reference is made to Remington: The Science and Practice of Pharmacy, 19th edition, 1995.

The formulations according to the invention may comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulations are a dried formulation (e.g. freeze-dried or spray-dried) ready for use without any prior dissolution.

In one embodiment the buffer may be selected from the group consisting of acetate, carbonate, citrate, glycylglycine, histidine, glycine, phosphate, hydrogen phosphate, and tris(hydroxymethyl)-aminomethan (TRIS), bicine, tricine, succinate, aspartic acid, asparagine or mixtures thereof.

In one embodiment the composition has a pH in the range of 5-10, such as 6-9, 6-8, 5-7, 7-9 or such as 5.5-7.5.

In a further embodiment of the invention the formulation further comprises a pharmaceutically acceptable preservative.

In a further embodiment of the invention the preservative is selected from the group consisting of phenol, m-cresol, methyl p-hydroxybenzoate, propyl p-hydroxybenzoate, 2-phenoxyethanol, benzyl alcohol, chlorobutanol, chlorocresol, benzethonium chloride1, or mixtures thereof. The use of a preservative in pharmaceutical compositions is well-known to the skilled person. For convenience reference is made to Remington: The Science and Practice of Pharmacy, 19th edition, 1995.

In a further embodiment of the invention the formulation further comprises an isotonic agent. The isotonic agent may be selected from the group consisting of a salt (e.g. sodium chloride), a sugar such as mono-, di-, or polysaccharides, or water-soluble glucans, including for example fructose, glucose, mannose, lactose, sucrose, trehalose, dextran, or sugar alcohol such as, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Sugar alcohol includes, for example, mannitol, sorbitol, inositol, galactitol, dulcitol, xylitol, and arabitol.

The use of an isotonic agent in pharmaceutical compositions is well-known to the skilled person. For convenience reference is made to Remington: The Science and Practice of Pharmacy, 19th edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, EGTA, and mixtures thereof.

In a further embodiment of the invention the formulation further comprises a stabilizer. The use of a stabilizer in pharmaceutical compositions is well-known to the skilled person. For convenience reference is made to Remington: The Science and Practice of Pharmacy, 19th edition, 1995

The pharmaceutical compositions of the invention may further comprise an amount of an amino acid base sufficient to decrease aggregate formation by the polypeptide or protein during storage of the composition. By "amino acid base" is intended an amino acid or a combination of amino acids, where any given amino acid is present either in its free base form or in its salt form. The amino acids may be arginine, lysine, aspartic acid, and glutamic acid, aminoguanidine, ornithine and N-monoethyl L-arginine, ethionine and buthionine and S-methyl-L cysteine.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

In a further embodiment of the invention the formulation further comprises a surfactant. Typical surfactants (with examples of trade names given in brackets [ ]) are polyoxyethylene sorbitan fatty acid esters such as polyoxyethylene (20) sorbitan monolaurate [Tween 20], polyoxyethylene (20) sorbitan monopalmitate [Tween 40] or polyoxyethylene (20) sorbitan monooleate [Tween 80], poloxamers such as polyoxypropylene-polyoxyethylene block copolymer [Pluronic F68/poloxamer 188], polyethylene glycol octylphenyl ether [Triton X-100] or polyoxyethyleneglycol dodecyl ether [Brij 35]. The use of a surfactant in pharmaceutical compositions is well-known to the skilled person. For convenience reference is made to Remington: The Science and Practice of Pharmacy, 19th edition, 1995.

In a specific embodiment Liraglutide may be administered in an aqueous solution comprising 5-10.0 mg/ml liraglutide, 1-2 mg/ml disodium phosphate dihydrate, 10-20 mg/ml propylene glycol and 2-8 mg/ml phenol.

In a specific embodiment Liraglutide may be administered in an aqueous solution consisting of 6.0 mg/ml liraglutide, 1.42 mg/ml disodium phosphate dihydrate, 14.0 mg/ml propylene glycol, 5.5 mg/ml phenol, and NaOH and/or HCl for adjustment of pH to 8.15.

In one embodiment, the present invention provides compositions comprising a GLP-1 agonist (e.g. GLP-1 peptide) and an inhibitor of IL-21 function. The GLP-1 agonist (e.g. GLP-1 peptide) and the inhibitor of IL-21 function may be comprised in a single composition or in separate compositions. In one embodiment the GLP-1 agonist and the inhibitor of IL-21 are provided in separate compositions. In one embodiment the invention provides a pharmaceutical composition that comprises one or more inhibitor of IL-21 function and/or GLP-1 agonists (such as a GLP-1 peptides) of the invention, formulated together with one or more pharmaceutically acceptable excipients. In one embodiment the compositions for use according to the invention are individually formulated to comprise different buffers and excipients suited for the GLP-1 agonist and IL-21 inhibitor, respectively.

In a further embodiment, the pharmaceutical composition comprises an aqueous solution of the an antibody, and a buffer, wherein the antibody is present in a concentration from 1 mg/ml or above (such as e.g. 1-200, 1-100, 50-200, 50-150, 50-100, 1, 5, 10, 15, 20, 25, 30, 35, 40, 45, 50, 60, 70, 80, 90, 100, 125, 150, 175, or 200 mg/ml) and wherein said composition has a pH from about 6.0 to about 8.0, such as e.g. about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0.

In one embodiment the antibody formulation includes histidine, sucrose, arginine, polysorbate and sodium chloride. Examples of high concentrate antibody formulation are known in the art and are described in such as WO 2011/104381.

In one embodiment the GLP-1 agonist (e.g. GLP-1 peptide) is formulated so as to have a half-life in man of at least 48 hours. This may be obtained by sustained release compositions known in the art.

Mode of Administration

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

The pharmaceutical compositions may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the [compound in the form of a nasal or pulmonal spray. As a still further option, the pharmaceutical compositions containing the [the protein] compound of the invention can also be adapted to transdermal administration, e.g. by needle-free injection or from a patch, optionally an iontophoretic patch, or transmucosal, e.g. buccal, administration.

The GLP-1 agonist (such as a GLP-1 peptide) and the inhibitor of IL-21 function of the invention may be administered separately or in combination, such as each in separate dosage forms or combined in a single dosage form.

The GLP-1 agonist (such as a GLP-1 peptide) and the inhibitor of IL-21 function of the invention may be administered concomitantly or sequentially.

In one embodiment the GLP-1 agonist and the inhibitor of IL-21 function are co-administered together with a further therapeutically active agent used in the treatments defined herein. In one embodiment said further therapeutically active agent is an insulin.

In one embodiment the route of administration of the GLP-1 agonist and/or the inhibitor of IL-21 of the invention may be any route which effectively transports the active compound to the appropriate or desired site of action, such as parenteral.

In one embodiment medicaments or pharmaceutical compositions comprising the GLP-1 agonist and/or the inhibitor of IL-21 of the invention may be administered parenterally to a patient in need thereof. In one embodiment parenteral administration may be performed by subcutaneous, intramuscular or intravenous injection by means of a syringe, optionally a pen-like syringe.

The GLP-1 agonist (e.g. GLP-1 peptide) and/or the inhibitor of IL-21 function of the invention may be administered parenterally, such as intravenously, such as intramuscularly, such as subcutaneously. In one embodiment the GLP-1 agonist (e.g. GLP-1 peptide) and/or the inhibitor of IL-21 function is administered by parenteral administration, such as subcutaneous injection. In one embodiment parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of a GLP-1 agonist in the form of a nasal or pulmonal spray. As a still further option, the GLP-1 agonist can also be administered transdermally or transmucosally, e.g., bucally.

Alternatively, the GLP-1 agonist (e.g. GLP-1 peptide) and/or the inhibitor of IL-21 of the invention may be administered via a non-parenteral route, such as perorally or topically. The GLP-1 agonist (e.g. GLP-1 peptide) and/or the inhibitor of IL-21 of the invention may be administered prophylactically. The GLP-1 agonist (e.g. GLP-1 peptide) and/or the inhibitor of IL-21 of the invention may be administered therapeutically (on demand).

In on embodiment the GLP-1 agonist is administered subcutaneously. In one embodiment the IL-21 inhibitor is administered intravenously or subcutaneously.

The frequency and dosages of the GLP-1 agonist and the IL-21 inhibitor will depend on multiple factors, in particular the half-life of the therapeutic and the bioavailability, depending on administration route, in the subject.

The GLP-1 agonists already used for the treatment of type 2 diabetes are administered once or twice daily. GLP-1 agonists with a further increase half-life are suited for once weekly administration. If possible even more seldom administration such as every 10 days or every fortnight (2 weeks) may be suited if the half-life and bioavailability support this. The dosage regime is adjusted based on general knowledge about GLP-1 agonist treatment. A lower start dosage may be used to reduce side effects.

Likewise IL-21 inhibitors may be for daily or weekly administration depending on half-life and bioavailability of the therapeutic in a given composition. In one embodiment the IL-21 inhibitor has an extended half-life, such as an antibody molecule and the administration is less frequent, such as monthly or at most every $4^{th}$ week. In one embodiment around 6-10 dosage unites are administered per year, such as a dosage unite every $4-8^{th}$ week, such as every $5-7^{th}$ week. In one embodiment the GLP-1 peptide is administered daily while the IL-21 inhibitor is administered every $6^{th}$ week.

In one embodiment as used herein, specific values given in relation to numbers or intervals may be understood as the specific value or as about the specific value.

Treatment and/or Prevention

Type 1 diabetes is a progressive autoimmune disease, wherein the body's ability to produce insulin is gradually decreased as the beta cells of the pancreas are destroyed.

Type 1 diabetes is considered a chronic disease which usually progresses rapidly to an insulin dependent stage e.g. the patient needs exogenous insulin to keep blood glucose low. The clinical diagnoses of type 1 diabetes mellitus (T1DM) or just type 1 diabetes (T1D) are:

HbA1c≥6.5% or fasting plasma glucose≥7.0 (126 mg/dL) or a 2 hour plasma glucose≥11.1 mmol/dL (200 mg/dL) during and oral glucose tolerance test with a glucose load of 75 grams anhydrous glucose in water or classical symptoms of hyperglycaemia and a random plasma glucose≥11.1 mm/L The classical treatment for type 1 diabetes is to supplement with exogenous insulin in order to replace the missing insulin and thereby obtain control of blood glucose. The healthy individual is able to adjust the level of blood glucose very tightly. Even with modern insulin products the diabetes patients have difficulties to obtain similarly well regulated blood glucose and the risk of hypoglycaemic and hyperglycaemic episodes remains.

The present invention relates to treatment and prevention of type 1 diabetes in a newly diagnosed individual. In one embodiment the individual has a non-fasting C-peptide of at least 0.2 nmol/L. In one embodiment the individual has a fasting C-peptide of at least 0.2 nmol/L. In one embodiment the individual the presence of one or more islet autoantibodies has been detected.

As described herein above the present invention relates to the treatment and/or prevention of type 1 diabetes by administration of an effective amount of a GLP-1 agonist, such as a GLP-1 peptide, and an effective amount of an inhibitor of IL-21 function. In the present case treatment and/or prevention does not necessarily refer to a complete cure or resistance to diabetes type 1 progression. The present invention relates to treatment of recently diagnosed type 1 diabetes patients or individual at risk of developing type 1 diabetes. As described above diabetes type 1 is a progressing disease in which the patient gradually loose the capability to produce sufficient insulin.

Most type 1 diabetes patients require insulin treatment and the method described herein allows for concomitant insulin treatment following normal guidance in order to achieve metabolic control.

In on embodiment the treatment preserves beta cell function. In one embodiment the treatment enhances endogenous insulin secretion.

In one embodiment beta cell function is preserved for at least one year, such as for at least two years from initiation of treatment.

Beta cell function e.g. the ability to produce insulin may be measured using standard techniques. In one embodiment the treatment increases the concentration of fasting C-peptide.

The C-peptide is released during the production of insulin. In healthy individuals the concentration of C-peptide is 0.5 to 2.7 nanograms per milliliter (ng/mL). While type 1 diabetes patients at the time of diagnosis produce some insulin and thus similar amounts of the C-peptide, this ability is usually lost within a relatively short period.

In some individuals with T1DM very small amount of insulin may be produced for an extended period of time (>10 years) after diagnose.

In one embodiment the C-peptide concentration is preserved for at least one year, such as for at least two years from initiation of treatment.

The ability to produce insulin may in one embodiment be measured in response to the mixed meal tolerance test (MMTT). In one such embodiment the amount of C-peptide is measured in the test and compared to the amount of C-peptide measured in response to the test before treatment. Parameters may be $AUC_{0-2h}$, $AUC_{0-4h}$ or Maximum MMX of C-peptide in the blood.

In one embodiment the decline in non-fasting C-peptide secretion is reduced compared to standard treatment. In one embodiment the decline in non-fasting C-peptide (MMTT) is reduced for at least one year or such as for two years compared to standard insulin treatment In one embodiment the level of non-fasting C-peptide is maintained from the start of treatment. In one embodiment the decline in non-fasting C-peptide from baseline (treatment initiation) is at most 10% after 1 year, or such as at most 5% after 1 year.

In one embodiment the treatment improves glycaemic control. In one embodiment the treatment and/or prevention according to the invention reduces the average blood glucose in the subject. The treatment may help the patients to reach treatment targets. In one embodiment the patients achieve an $HbA_{1c}$ lower than usually obtained using standard treatment. The general target for diabetes patients is to keep $HbA_{1c}$ below 6.5%. In one embodiment the treatment reduces $HbA_{1c}$ within the treatment period. In one embodiment the treatment reduces $HbA_{1c}$ for a prolonged period. In one embodiment more patients obtain and $HbA_{1c}$ below 6.5% (compared to standard treatment).

In one embodiment the treatment improves the fasting plasma glucose compared to the measures of fasting plasma glucose prior to treatment. In one embodiment the treatment improves the fasting plasma glucose compared to the average reached using standard insulin treatment.

In one embodiment the treatment extends the period where the subject produces endogenous insulin. The treatment may thus postpone the time point where the subject needs (exogenous) insulin and/or reduce the amount of needed (exogenous) insulin. This treatment may thus delay progression of Beta cell destruction and reduce the dependence on exogenous insulin. In one embodiment treatment reduces the dependence on exogenous insulin.

In one embodiment the treatment and/or prevention according to the invention allow the subject to reduce the amount of exogenous insulin e.g. insulin injections.

In one embodiment the treatment reduces fasting plasma glucose. In one embodiment the treatment reduces insulitis.

In one embodiment the treatment is observed within a time frame of 1-4 weeks or 1-6 months. As type 1 diabetes is understood to be a progressing chronic disease, the observed effect should preferably be maintained for up to a year or two. In one embodiment the treatment preserves Beta cell function for 6, 12, 18 or 24 weeks. In one embodiment the treatment preserves Beta cell function for 36, 42, 48 or 52 weeks.

In one embodiment the majority of patients maintain Beta cell function for at least a year. In one embodiment the majority of patients maintain Beta cell function for at least two years.

In one embodiment the treatment allows the patient to reduce the amount of exogenous insulin either by reducing the daily dosage (units/kg calculated as average over three days) or the number of insulin injections administered per day (three day average). In one embodiment the treatment reduces insulin requirement for 6, 12, 18 or 24 weeks. In one embodiment the treatment reduces insulin requirement for 36, 42, 48 or 52 weeks.

In on embodiment the invention relates to a method of treatment and/or prevention of type 1 diabetes comprising administration of an effective amount of a GLP-1 agonist and an effective amount an IL-21 inhibitor to a patient in need thereof. As described above the two compounds maybe administered separately while it is to be understood that it is the combined dosage of the GLP-1 and the IL-21 inhibitor that are effective in treatment of type 1 diabetes as described herein.

In one embodiment the invention relates to a method of treatment of type 1 diabetes comprising administration of an amount of an GLP-1 agonist and an amount of IL-21 function that in combination are effective, to a subject in need.

Depending on the identity of the GLP-1 and IL-21 inhibitor the exact dosage may be adjusted. Depending of the half-life of the products dosage and dosage frequency may be adjusted.

For GLP-1 peptide derivatives, such as liraglutide a dosage of 0.01-100 mg, such as 0.1-1.8 mg, is administered per dosage unit. In one embodiment 0.5 mg to 2 mg is administered be dosage unit. In general one daily dosage is administered. For GLP-1 agonists (including GLP-1 peptides) with extended half-life administrations may be twice or once weekly. If bioavailability is extended even one monthly administration can be foreseen.

For antibody IL-21 inhibitors, a dosage of 5-20 mg/kg is administered per dosage unit. In one embodiment 10-15 mg/kg is administered. Antibody products are usually administered less frequently than the GLP-1 agonist, such as at most once a week. In one embodiment the antibody IL-21 inhibitor is administered every 4-10$^{th}$ week, such as every 4-8$^{th}$ week, such as every 6$^{th}$ week. In one embodiment 12 mg/kg of the anti-Il-21 antibody is administered every 6$^{th}$ week.

While certain features of the invention are described and illustrated herein, many modifications, substitutions, changes, and equivalents will now occur to those of ordinary skill in the art. It is, therefore, to be understood that the application is intended to cover all such modifications and changes as fall within the true spirit of the invention. The accompanying embodiments and claims are not to be construed as limiting of the invention.

EMBODIMENTS OF THE INVENTION

1. Use of a GLP-1 agonist, such as a GLP-1 peptide, and an inhibitor of IL-21 function for the treatment and/or prevention of type 1 diabetes.
2. Use according to any of the preceding embodiments, wherein said inhibitor neutralizes IL-21 function.
3. Use according to any one of the preceding embodiments, wherein said inhibitor of IL-21 function is an antibody that is capable of specifically binding IL-21.
4. Use according to any one of the preceding embodiments, wherein said inhibitor of IL-21 function is an anti-IL-21 antibody.
5. Use according to any one of the preceding embodiments, wherein said inhibitor of IL-21 function competes with a receptor for binding to IL-21, wherein said receptor is selected from the list consisting of: IL-21Rα and γC.
6. Use according to any one of the preceding embodiments, wherein said inhibitor of IL-21 function competes with IL-21Rα for binding to IL-21.
7. Use according to any one of the preceding embodiments, wherein said inhibitor of IL-21 function binds to helix 1 and 3 of human IL-21.
8. Use according to any one of the preceding embodiments, wherein said inhibitor of IL-21 function binds to a discontinuous epitope on IL-21, wherein said epitope comprises amino acids I37 to Y52 and N92 to P108 as set forth in SEQ ID NO 1.
9. Use according to any one of the preceding embodiments, wherein said inhibitor of IL-21 function comprises the three CDR sequences as set forth in SEQ ID NO 2 and the three CDR sequences as set forth in SEQ ID NO 3.
10. Use according to any one of the preceding embodiments, wherein said inhibitor of IL-21 function is an anti-IL-21 antibody that competes with γC for binding to IL-21.
11. Use according to any one of the preceding embodiments, wherein said inhibitor of IL-21 function binds to helix 2 and 4 of human IL-21.
12. Use according to any one of the preceding embodiments, wherein said inhibitor of IL-21 function binds to an epitope comprising amino acids Glu 65, Asp 66, Val 67, Glu 68, Thr 69, Asn 70, Glu 72, Trp 73, Lys 117, His 118, Arg 119, Leu 143, Lys 146, Met 147, His 149, Gln 150, and His 151 as set forth in SEQ ID NO 1
13. Use according to any one of the preceding embodiments, wherein said inhibitor of IL-21 function comprises the three CDR sequences as set forth in SEQ ID NO 4 and the three CDR sequences as set forth in SEQ ID NO 5.
14. Use according to any one of the preceding embodiments, wherein said inhibitor of IL-21 function specifically binds to IL-21 with a binding affinity of $10^7$ M$^{-1}$ or greater, $10^8$ M$^{-1}$ or greater, $10^9$ M$^{-1}$ or greater, $10^{10}$ M$^{-1}$ or greater, $10^{10}$ M$^{-1}$ or greater, or $10^{12}$ M$^{-1}$ or greater.
15. Use according to any one of the preceding embodiments, wherein said GLP-1 peptide is liraglutide.

16. Use according to any one of the preceding embodiments, wherein said GLP-1 agonist and said inhibitor of IL-21 function are administered concomitantly or sequentially.
17. Use according to any one of the preceding embodiments, wherein said GLP-1 agonist is administered daily while the IL-21 inhibitor is administered every 6$^{th}$, week.
18. Use according to any one of the preceding embodiments, wherein said GLP-1 agonist and said inhibitor of IL-21 function are administered to a subject with recently diagnosed type 1 diabetes.
19. Use according to any one of the preceding embodiments, wherein said GLP-1 agonist and said inhibitor of IL-21 function are administered to a subject having a non-fasting C-peptide of at least 0.2 nmol/L.
20. Use according to any one of the preceding embodiments, wherein said GLP-1 agonist and said inhibitor of IL-21 function are administered to a subject at risk of developing type 1 diabetes, such as subjects with islet autoantibodies or subjects genetically at-risk without islet autoantibodies.
21. Use according to any one of the preceding embodiments wherein beta-cell function is preserved for at least one year from treatment initiation.
22. Use according to any one of the preceding embodiments wherein the average daily insulin requirement is reduced compared to standard insulin treatment.
23. Use according to any one of the preceding embodiments, wherein 0.01-100 mg, such as 0.1-1.8 mg, GLP-1 agonist, such as a GLP-1 peptide, is administered per dosage unit.
24. Use according to any one of the preceding embodiments, wherein said GLP-1 agonist and said inhibitor of IL-21 function are comprised in a composition optionally comprising one or more additional excipients.
25. Use according to any one of the preceding embodiments, wherein said GLP-1 agonist and said inhibitor of IL-21 function are comprised by separate pharmaceutical compositions optionally comprising one or more additional excipients.
26. Use according to any one of the preceding embodiments, wherein said composition(s) is in the form of an aqueous composition or a freeze-dried composition.
27. Use according to any one of the preceding embodiments, wherein said composition(s) has a pH in the range of 5-10, such as 6-8.
28. A method for the treatment and/or prevention of type 1 diabetes comprising administration of a GLP-1 agonist, such as a GLP-1 peptide, and an inhibitor of IL-21 function to a patient in need thereof.
29. The method according to any one of the preceding embodiments, wherein said inhibitor neutralizes IL-21 function.
30. The method according to any one of the preceding embodiments, wherein said inhibitor of IL-21 function is an antibody that is capable of specifically binding IL-21.
31. The method according to any one of the preceding embodiments, wherein said inhibitor of IL-21 function is an anti-IL-21 antibody.
32. The method according to any one of the preceding embodiments, wherein said inhibitor of IL-21 function competes with a receptor for binding to IL-21, wherein said receptor is selected from the list consisting of: IL-21Rα and γC.
33. The method according to any one of the preceding embodiments, wherein said inhibitor of IL-21 function competes with IL-21Rα for binding to IL-21.
34. The method according to any one of the preceding embodiments, wherein said inhibitor of IL-21 function binds to helix 1 and 3 of human IL-21.
35. The method according to any one of the preceding embodiments, wherein said inhibitor of IL-21 function binds to a discontinuous epitope on IL-21, wherein said epitope comprises amino acids I37 to Y52 and N92 to P108 as set forth in SEQ ID NO 1.
36. The method according to any one of the preceding embodiments, wherein said inhibitor of IL-21 function comprises the three CDR sequences as set forth in SEQ ID NO 2 and the three CDR sequences as set forth in SEQ ID NO 3.
37. The method according to any one of the preceding embodiments, wherein said inhibitor of IL-21 function is an anti-IL-21 antibody that competes with γC for binding to IL-21.
38. The method according to any one of the preceding embodiments, wherein said inhibitor of IL-21 function binds to helix 2 and 4 of human IL-21.
39. The method according to any one of the preceding embodiments, wherein said inhibitor of IL-21 function binds to an epitope comprising amino acids Glu 65, Asp 66, Val 67, Glu 68, Thr 69, Asn 70, Glu 72, Trp 73, Lys 117, His 118, Arg 119, Leu 143, Lys 146, Met 147, His 149, Gln 150, and His 151 as set forth in SEQ ID NO 1.
40. The method according to any one of the preceding embodiments, wherein said inhibitor of IL-21 function comprises the three CDR sequences as set forth in SEQ ID NO 4 and the three CDR sequences as set forth in SEQ ID NO 5.
41. The method according to any one of the preceding embodiments, wherein said inhibitor of IL-21 function specifically binds to IL-21 with a binding affinity of $10^7$ M$^{-1}$ or greater, $10^8$ M$^{-1}$ or greater, $10^9$ M$^{-1}$ or greater, $10^{10}$ M$^{-1}$ or greater, $10^{10}$ M$^{-1}$ or greater, or $10^{12}$ M$^{-1}$ or greater.
42. The method according to any one of the preceding embodiments, wherein said GLP-1 agonist is liraglutide.
43. The method according to any one of the preceding embodiments, wherein said GLP-1 agonist and said inhibitor of IL-21 function are administered concomitantly or sequentially.
44. The method according to any one of the preceding embodiments, wherein said GLP-1 agonist is administered daily while the IL-21 inhibitor is administered every 6$^{th}$, week.
45. The method according to any one of the preceding embodiments, wherein said GLP-1 agonist and said inhibitor of IL-21 function are administered to a subject with recently diagnosed type 1 diabetes.
46. The method according to any one of the preceding embodiments, wherein said GLP-1 agonist and said inhibitor of IL-21 function are administered to a subject having a non-fasting C-peptide concentration of at least 0.2 nmol/L.
47. The method according to any one of the preceding embodiments, wherein said GLP-1 agonist and said inhibitor of IL-21 function are administered to a subject at risk of developing type 1 diabetes, such as subjects with islet autoantibodies or subjects genetically at-risk without islet autoantibodies.
48. The method according to any of the preceding embodiment for the treatment and/or prevention of type 1 diabetes comprising administration of an effective amount of a GLP-1 agonist and an inhibitor of IL-21 function to a patient in need thereof.

49. The method according to any of the preceding embodiment for the treatment and/or prevention of type 1 diabetes comprising administration of an effective amount of a GLP-1 agonist and an inhibitor of IL-21 function to a patient in need thereof, wherein the decline in non-fasting C-peptide secretion is reduced compared to standard treatment. The method according to any of the preceding embodiment for the treatment and/or prevention of type 1 diabetes comprising administration of an effective amount of a GLP-1 agonist and an inhibitor of IL-21 function to a patient in need thereof, wherein beta cell function is preserved for at least one year from treatment initiation.
50. The method according to any of the preceding embodiment for the treatment and/or prevention of type 1 diabetes comprising administration of an effective amount of a GLP-1 agonist and an inhibitor of IL-21 function to a patient in need thereof, wherein the average daily insulin requirement is reduced compared to standard insulin treatment.
51. The method according to any one of the preceding embodiments, wherein 0.01-100 mg, such as 0.1-1.8 mg, GLP-1 agonist, such as a GLP-1 peptide, is administered per dosage unit.
52. The method according to any one of the preceding embodiments, wherein said GLP-1 agonist and said inhibitor of IL-21 function are comprised by separate pharmaceutical compositions optionally comprising one or more additional excipients.
53. The method according to any one of the preceding embodiments, wherein said composition(s) is in the form of an aqueous composition or a freeze-dried composition.
54. The method according to any one of the preceding embodiments, wherein said composition(s) has a pH in the range of 5-10, such as 6-8.
55. A GLP-1 agonist, such as a GLP-1 peptide, and an inhibitor of IL-21 function for use in the manufacture of one or more medicaments for the treatment and/or prevention of type 1 diabetes.
56. A GLP-1 agonist, such as a GLP-1 peptide, and an inhibitor of IL-21 function for use in a method of treatment and/or prevention of type 1 diabetes.
57. The GLP-1 agonist and inhibitor of IL-21 function according to any one of the preceding embodiments, wherein said inhibitor neutralizes IL-21 function.
58. The GLP-1 agonist and inhibitor of IL-21 function according to any one of the preceding embodiments, wherein said inhibitor of IL-21 function is an antibody that is capable of specifically binding IL-21.
59. The GLP-1 agonist and inhibitor of IL-21 function according to any one of the preceding embodiments, wherein said inhibitor of IL-21 function is an anti-IL-21 antibody.
60. The GLP-1 agonist and inhibitor of IL-21 function according to any one of the preceding embodiments, wherein said inhibitor of IL-21 function competes with a receptor for binding to IL-21, wherein said receptor is selected from the list consisting of: IL-21Rα and γC.
61. The GLP-1 agonist and inhibitor of IL-21 function according to any one of the preceding embodiments, wherein said inhibitor of IL-21 function competes with IL-21Rα for binding to IL-21.
62. The GLP-1 agonist and inhibitor of IL-21 function according to any one of the preceding embodiments, wherein said inhibitor of IL-21 function binds to helix 1 and 3 of human IL-21.
63. The GLP-1 agonist and inhibitor of IL-21 function according to any one of the preceding embodiments, wherein said inhibitor of IL-21 function binds to a discontinuous epitope on IL-21, wherein said epitope comprises amino acids I37 to Y52 and N92 to P108 as set forth in SEQ ID NO 1.
64. The GLP-1 agonist and inhibitor of IL-21 function according to any one of the preceding embodiments, wherein said inhibitor of IL-21 function comprises the three CDR sequences as set forth in SEQ ID NO 2 and the three CDR sequences as set forth in SEQ ID NO 3.
65. The GLP-1 agonist and inhibitor of IL-21 function according to any one of the preceding embodiments, wherein said inhibitor of IL-21 function is an anti-IL-21 antibody that competes with γC for binding to IL-21.
66. The GLP-1 agonist and inhibitor of IL-21 function according to any one of the preceding embodiments, wherein said inhibitor of IL-21 function binds to helix 2 and 4 of human IL-21.
67. The GLP-1 agonist and inhibitor of IL-21 function according to any one of the preceding embodiments, wherein said inhibitor of IL-21 function binds to an epitope comprising amino acids Glu 65, Asp 66, Val 67, Glu 68, Thr 69, Asn 70, Glu 72, Trp 73, Lys 117, His 118, Arg 119, Leu 143, Lys 146, Met 147, His 149, Gln 150, and His 151 as set forth in SEQ ID NO 1.
68. The GLP-1 agonist and inhibitor of IL-21 function according to any one of the preceding embodiments, wherein said inhibitor of IL-21 function comprises the three CDR sequences as set forth in SEQ ID NO 4 and the three CDR sequences as set forth in SEQ ID NO 5.
69. The GLP-1 agonist and inhibitor of IL-21 function according to any one of the preceding embodiments, wherein said inhibitor of IL-21 function specifically binds to IL-21 with a binding affinity of $10^7$ $M^{-1}$ or greater, $10^8$ $M^{-1}$ or greater, $10^9$ $M^{-1}$ or greater, $10^{10}$ $M^{-1}$ or greater, $10^{10}$ $M^{-1}$ or greater, or $10^{12}$ $M^{-1}$ or greater.
70. The GLP-1 agonist and inhibitor of IL-21 function according to any one of the preceding embodiments, wherein said GLP-1 agonist is liraglutide.
71. The GLP-1 agonist and inhibitor of IL-21 function according to any one of the preceding embodiments, wherein said GLP-1 agonist, and said inhibitor of IL-21 function are administered concomitantly or sequentially.
72. The GLP-1 agonist and inhibitor of IL-21 function according to any one of the preceding embodiments, wherein said GLP-1 agonist is administered daily while the IL-21 inhibitor is administered every $6^{th}$ week.
73. The GLP-1 agonist and inhibitor of IL-21 function according to any one of the preceding embodiments, wherein said GLP-1 agonist, and said inhibitor of IL-21 function are administered to a subject recently diagnosed with type 1 diabetes.
74. The method according to any one of the preceding embodiments, wherein said GLP-1 agonist and said inhibitor of IL-21 function are administered to a subject having a non-fasting C-peptide concentration of at least 0.2 nmol/L.
75. The GLP-1 agonist and inhibitor of IL-21 function according to any one of the preceding embodiments, wherein said GLP-1 agonist, and said inhibitor of IL-21 function are administered to a subject at risk of developing type 1 diabetes, such as subjects with islet autoantibodies or subjects genetically at-risk without islet autoantibodies.
76. The GLP-1 agonist and inhibitor of IL-21 function according to any of the preceding embodiments, wherein beta cell function is preserved for at least one year from treatment initiation.

77. The GLP-1 agonist and inhibitor of IL-21 function according to any of the preceding embodiments, wherein the average daily insulin requirement is reduced compared to standard insulin treatment.
78. The GLP-1 agonist and inhibitor of IL-21 function according to any one of the preceding embodiments, wherein 0.01-100 mg, such as 0.1-1.8 mg, GLP-1 agonist, is administered per dosage unit.
79. The GLP-1 agonist and inhibitor of IL-21 function according to any one of the preceding embodiments, wherein said GLP-1 agonist, and said inhibitor of IL-21 function are comprised in a composition optionally comprising one or more additional excipients.
80. The GLP-1 agonist and inhibitor of IL-21 function according to any one of the preceding embodiments wherein said GLP-1 agonist and said inhibitor of IL-21 function are comprised by separate pharmaceutical compositions optionally comprising one or more additional excipients.
81. The GLP-1 agonist and inhibitor of IL-21 function according to any one of the preceding embodiments, wherein said composition(s) is in the form of an aqueous composition or a freeze-dried composition.
82. The GLP-1 agonist, such as a GLP-1 peptide, and inhibitor of IL-21 function according to any one of the preceding embodiments, wherein said composition(s) has a pH in the range of 5-10, such as 6-8.

EXAMPLES

Materials and Methods

The GLP-1 peptide liraglutide is commercially available and may be produced as described in Example 37 of WO98/08871. Anti-IL-21 antibody may be produced as described in Example 1 of WO2010/055366, e.g. by immunisation with human IL-21 or mouse IL-21 and the neutralizing activity characterized as described in subsequent examples therein.

Assay (I): In Vitro Potency of GLP-1 Agonists, Such as a GLP-1 Peptides

The purpose of this example is to test the activity, or potency, of GLP-1 agonists (e.g. GLP-1 peptides) in vitro. The potencies of GLP-1 agonists (e.g. GLP-1 peptides) may be determined as described below, i.e. as the stimulation of the formation of cyclic AMP (cAMP) in a medium containing membranes expressing the human GLP-1 receptor.

Principle:

Purified plasma membranes from a stable transfected cell line, BHK467-12A (tk-ts13), expressing the human GLP-1 receptor are stimulated with the GLP-1 agnoist (e.g. GLP-1 peptide) in question, and the potency of cAMP production is measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes:

A stable transfected cell line and a high expressing clone are selected for screening. The cells are grown at 5% CO2 in DMEM, 5% FCS, 1% Pen/Strep (Penicillin/Streptomycin) and 0.5 mg/ml of the selection marker G418. Cells at approximate 80% confluence are washed 2× with PBS and harvested with Versene (aqueous solution of the tetrasodium salt of ethylenediaminetetraacetic acid), centrifuged 5 min at 1000 rpm and the supernatant removed. The additional steps are all made on ice. The cell pellet is homogenised by the Ultrathurax for 20-30 sec. in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension is homogenised for 20-30 sec and centrifuged 15 min at 20,000 rpm. Suspension in Buffer 2, homogenisation and centrifugation is repeated once and the membranes are resuspended in Buffer 2. The protein concentration is determined and the membranes stored at −80° C. until use. The assay is performed in/h-area 96-well plates, flat bottom (e.g. Costar cat. no:3693). The final volume per well is 50 µl.

Solutions and Reagents:

Exemplary solutions and reagents are given below.

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat. no: T3253); 5 mM HEPES (Sigma, cat. no: H3375); 10 mM MgCl2, 6H2O (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 µM.

cAMP standard (dilution factor in assay=5): cAMP Solution: 5 µL of a 5 mM cAMP-stock+495 µL AlphaScreen Buffer.

Suitable dilution series in AlphaScreen Buffer are prepared of the cAMP standard as well as the GLP-1 agonist, such as the GLP-1 peptide, to be tested, e.g. the following eight concentrations of the GLP-1 agonist, such as the GLP-1 peptide: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3\times10^{-11}$ of CAMP.

Membrane/Acceptor Beads:

Use hGLP-1/BHK 467-12A membranes; 6 µg/well corresponding to 0.6 mg/ml (the amount of membranes used per well may vary). "No membranes": Acceptor Beads (15 µg/ml final) in AlphaScreen buffer. "6 µg/well membranes": membranes+Acceptor Beads (15 µg/ml final) in AlphaScreen buffer. Add 10 µl "No membranes" to cAMP standard (per well in duplicates) and the positive and negative controls. Add 10 µl "6 µg/well membranes" to GLP-1 and GLP-1 agonists (e.g. GLP-1 peptides) (per well in duplicates/triplicates). Pos. Control: 10 µl "no membranes"+10 µl AlphaScreen Buffer. Neg. Control: 10 µl "no membranes"+10 µl cAMP Stock Solution (50 µM). As the beads are sensitive to direct light, any handling is in the dark (as dark as possible), or in green light. All dilutions are made on ice.

Procedure:

1) Make the AlphaScreen Buffer. 2) Dissolve and dilute the GLP-1 agonists/cAMP standard (e.g. GLP-1 peptides/cAMP standard) in AlphaScreen Buffer. 3) Make the Donor Beads solution and incubate 30 min. at RT. 4) Add the cAMP/GLP-1 agonists (e.g. cAMP/GLP-1 peptides) to the plate: 10 µl per well. 5) Prepare membrane/Acceptor Beads solution and add this to the plates: 10 µl per well. 6) Add the Donor Beads: 30 µl per well. 7) Wrap the plate in aluminum foil and incubate on the shaker for 3 hours (very slowly) at RT. 8) Count on AlphaScreen—each plate pre incubates in the AlphaScreen for 3 minutes before counting. The EC50 [pM] values may be calculated using the Graph-Pad Prism software (version 5). If desired, the fold variation in relation to GLP-1 may be calculated as EC50 (GLP-1)/EC50 (analogue)–3693.2.

Assay (II): Half-Life of GLP-1 Agonists (e.g. GLP-1 Peptides) in Minipigs

The purpose of this study is to determine the protraction in vivo of GLP-1 agnosits (e.g. GLP-1 peptides) after i.v. administration to minipigs, i.e. the prolongation of their time of action. This is done in a pharmacokinetic (PK) study, where the terminal half-life of the GLP-1 agonist, such as the GLP-1 peptide, in question is determined. By terminal half-life is generally meant the period of time it takes to halve a certain plasma concentration, measured after the initial distribution phase.

Male Göttingen minipigs are obtained from Ellegaard Göttingen Minipigs (Dalmose, Denmark) approximately 7-14 months of age and weighing from approximately 16-35 kg are used in the studies. The minipigs are housed individually and fed restrictedly once or twice daily with SDS minipig diet (Special Diets Services, Essex, UK). After at least 2 weeks of acclimatization two permanent central venous catheters are implanted in vena cava caudalis or cranialis in each animal. The animals are allowed 1 week recovery after the surgery, and are then used for repeated pharmacokinetic studies with a suitable wash-out period between dosings.

The animals are fasted for approximately 18 h before dosing and for at least 4 h after dosing, but have ad libitum access to water during the whole period.

The GLP-1 agonist, such as the GLP-1 peptide, is dissolved in 50 mM sodium phosphate, 145 mM sodium chloride, 0.05% tween 80, pH 7.4 to a concentration of usually from 20-60 nmol/ml. Intravenous injections (the volume corresponding to usually 1-2 nmol/kg, for example 0.033 ml/kg) of the compounds are given through one catheter, and blood is sampled at predefined time points for up till 13 days post dosing (preferably through the other catheter). Blood samples (for example 0.8 ml) are collected in EDTA buffer (8 mM) and then centrifuged at 4° C. and 1942G for 10 minutes. Plasma is pippetted into Micronic tubes on dry ice, and kept at −20° C. until analyzed for plasma concentration of the respective GLP-1 compound using ELISA or a similar antibody based assay or LC-MS. Individual plasma concentration-time profiles are analyzed by a non-compartmental model in WinNonlin v. 5.0 (Pharsight Inc., Mountain View, Calif., USA), and the resulting terminal half-lives (harmonic mean) determined.

Assay (III): Inhibition of IL-21 Mediated STAT-3 Phosphorylation.

The ability of anti-IL-21 antibodies to neutralize IL-21 can be measured in a cell based assay using phosphorylation of STAT3 as read-out. BaF3 cells transfected with IL-21 receptor (IL-21R) are used and as IL-21 induces STAT3 phosphorylation reduction hereof by an anti-IL-21 antibody reflects the IL-21 neutralization activity.

Reduction in murine IL-21 activity in the presence of antibody containing supernatant was determined by measuring the level of STAT3-phosphorylation following ligand-receptor interaction in BaF3/KZ134/hIL-21R cells.

Relative neutralization activity was determined based on the percentage decrease in phosphorylated-STAT3 levels relative to control cells incubated with ligand alone. Baf3/KZ134/hIL-21R cells are plated in 96-well round-bottom tissue culture plates at a density of 50,000 cells/well. Murine IL-21 was pre-incubated with the supernatant from each tested well before transfer to the plated cells. The reactions were stopped and cells lyzed according to the manufacturer's instructions, (BIO-RAD Laboratories). Supernatants were collected, mixed with assay buffer and stored. Capture beads (BIO-PLEX Phospho-STAT3 Assay, BIO-RAD Laboratories) were plated in 96-well filter plates and mixed with cell lysate samples and incubated according to the manufacturer's instructions (BIO-RAD Laboratories). Detection antibody (BIORAD laboratories) and streptavidin-PE was added and the reactions were resuspended in Resuspension Buffer (BIO-RAD Laboratories). The level of phosphorylated-STAT3 was determined on an array reader (BIO-PLEX, BIO-RAD Laboratories) according to the manufacturer's instructions. Increases in the level of the phosphorylated STAT3 transcription factor in the lysates were indicative of a mouse IL-21 receptor-ligand interaction. For the neutralization assay, decreases in the level of the phosphorylated STAT3 transcription factor were indicative of mAbs capable of neutralizing the IL-21 receptor-ligand interaction.

Assay (IV): Inhibition of IL-21-Driven B Cell Proliferation.

As a functionality test, anti-mIL-21 is tested for its ability to neutralize mIL-21-driven B cell proliferation. Equivalent assays may be performed for testing of anti-hIL-21 antibodies, such as Example 10 of WO2013/164021 that utilizes PBMC's isolated from healthy human volunteers. Further information on ability to inhibit B-cell maturation may be obtained as described in Example 6 and 12 of WO2012/098113.

Materials

Plates: U-bottomed 96-well plate (Corning Costar #3894)

Complete media: RPMI with GlutaMAX (cat no. 61870), 0.5 mM Sodium, Pyruvate, 5 ml non-essential amino acids (100×), 50 µM 2-ME, Pen/Strep and 10% HI FBS.

Purified Anti-CD40: BD#553787:

Purified Anti-IgM: Jackson #115-006-020

CD45R (B220) Microbeads: Miltenyi Biotec 130-049-501

3H-thymidine: Amersham, TRK-565.

Test and Control Materials

Mouse anti-mIL-21 mAb, done 397.18.2.1

Recombinant mouse IL-21 (rmIL-21)

Mouse IgG1 Isotype (Anti-TNP)

Mouse B cells are purified from spleens harvested from 6-8 weeks old wild-type C57BL/6 mice. Single cell splenocytes are prepared by forcing the organ through a 70 µm cell strainer into PBS. B cells were purified by anti-B220 positive selection by magnetic beads, using magnetic beads and an AutoMACS cell separator (Miltenyi Biotec) according to manufacturer's protocol.

Cells are stimulated in vitro with: a) soluble anti-IgM (1 µg/mL), b) soluble anti-CD40 (1 µg/mL) and c) mIL-21 (25, 50, 100 ng/mL). $10^5$ purified B cells were added per well in a 96-well-plate and stimulated for 72 h at 37° C. with soluble IgM (1 µg/mL), soluble anti-CD40 IgM (1 µg/mL) and rmIL-21 (100 ng/mL) in the presence of an anti-IL-21 antibody or an isotype control antibody. For the last 18 h of incubation 3H-thymidine is added to each well and thymidine-incorporation (proliferation) was measured on a Top Counter liquid scintilator (Perkin Elmer)

The results have demonstrated that the anti-mIL-21 antibody is capable of inhibiting B-cell proliferation in a concentration dependent manner.

Assay (V): Determination of Blood Glucose Effect in NOD Model

The purpose of this experiment was to determine the effect of administration of a GLP-1 agonist, such as the GLP-1 peptide, and/or an inhibitor of IL-21 function on blood glucose.

The recent-onset NOD mouse model was used. Mice were screened twice weekly and diabetes onset was defined as 2 consecutive blood glucose values of >250 mg/dL. Mice were enrolled into the experiment starting at 11 weeks of age and continued to be enrolled through 26 weeks of age. Dosing was weight based.

Blood glucose was measured by using a blood glucose meter (Bayer Contour USB) with the corresponding blood glucose strips. Mice with a blood glucose level>250 mg/dL on two consecutive days were considered diabetic. When high blood glucose was observed for the first time, blood glucose was measured again the following day. If the measurement was again >250 mg/dL, the animal was recorded as diabetic, enrolled into a treatment group, and was monitored further until it reached two consecutive readings of >600 mg/dL. At this time the mouse was sacrificed. Mice were also sacrificed before they reached a blood glucose value of >600 mg/dL if their overall condition was deteriorating, as determined by weight and/or overall appearance. If the second measurement did not confirm the onset of diabetes (i.e. is <250 mg/dL), the animal was left until the next regular measurement, and the procedure above was repeated.

Example 1—Liraglutide in Combination with Anti-IL-21 in the NOD Model

The purpose of this experiment was to determine the effect of the combination of anti-IL-21 antibody and liraglutide on blood glucose. It was tested whether a short course of mouse surrogate anti-IL-21 antibody in combination with daily liraglutide administration could reverse hyperglycemia. The mouse surrogate anti-IL-21 antibody was prepared by immunization of 6 to 8 week old BALB/c mice by s.c. injection with recombinant mouse IL-21 in a mixture of adjuvants. Recombinant mouse IL-21 is commercially available and has the sequence MHKSSPQGPD RLLIRLRHLI DIVEQLKIYE NDLDPELLSA PQDVK-GHCEH AAFACFQKAK LKPSNPGNNK TFIIDLVAQL RRRLPARRGG KKQKHIAKCP SCDSYEKRTP KEFLERLKWL LQKMIHQHLS (SEQ ID No 13). Initially antibody clones binding mIL-21 were selected using a standard capture style ELISA assay and a clone with strong neutralizing activity as determined by the STAT3 phosphorylation assay describe above was subsequently selected.

The experiment was carried out as described in Assay (V) herein, wherein the experimental details were as follows: Treatment groups were the following: (1) untreated; (2) Anti-IL-21 25 mg/kg, 5 administrations; (3) liraglutide 1 mg/kg daily for 5 weeks; and (4) Anti-IL-21 25 mg/kg, 5 administrations+liraglutide 1 mg/kg daily for 5 weeks. Anti-IL-21 was administered i.p. five times twice weekly starting immediately after inclusion of mice, i.e. from Day 0. Liraglutide was administered s.c. in its marketed composition with a ramp-up of 0.3 mg/kg on Day 0, 0.6 mg/kg on Day 1, and then 1 mg/kg on Day 2 and thereafter. The liraglutide treatment was carried out days 0-35 post diabetes onset; blood glucose was monitored for an additional 35 days, twice weekly. Mouse surrogate anti-IL-21 is an mIgG1/kappa isotype with the VL amino acid sequence: MDFQVQ-IFSFLLISASVILSRGQTVLIQSPAIMSASPGEKVTMTC-SASSSVSYMH WYQQKSGTSPKRWIYDTSKLASGVPARFSGSGSGT-SYSLTISSMEAEDAATYYCQ QWNSNPPTFGGGT-KLEMK (SEQ ID NO:26), and the VH amino acid sequence: MNFGPSLIFLVLILKGVQCEVQLVES-GGGLVKPGGSLKLSCAASGFTFNRYSMSW VRQS-PEKRLEWVAEISVGGSYTQYVDIVTGRFTISRD-NAKNTLYLEMSSLRSEDT AMYYCARLYYSGSGDSYYYAMDYWGQGTSVTVSS (SEQ ID NO:27). The stock concentration of anti-IL-21 was 11 mg/ml in 20 mM phosphate, 150 mM NaCl at pH=7.4; endotoxin levels were <0.01 EU/mg and purity is >95% and long term storage was done at −80° C. Before use, anti-IL-21 was diluted in buffer (20 mM phosphate, 150 mM NaCl, pH=7.4). Aliquots of anti-IL-21 for injection into the animals were only thawed once. The results are shown in Table 1 and FIG. 1-2.

TABLE 1

Average blood glucose (mg/dL) +/− SD (standard deviation) following administration of liraglutide and/or anti-IL-21 in the NOD model (N = 10 per group at onset. Over the course of the experiment, some animals were removed from the study and euthanized due to high blood glucose values (above 600 mg/dL) and/or poor general health. Remaining n is indicated in the table). The time period shown runs through the liraglutide treatment phase (days 0-35 post diabetes onset) and an additional 35 days of monitoring. Limit of detection for the glucose meter was 600 mg/dL.

| Time (days post diabetes onset) | Untreated control | Anti-IL-21 alone | Liraglutide alone | Liraglutide and Anti-IL-21* |
|---|---|---|---|---|
| 0  | 375 +/− 91         | 351 +/− 56          | 374 +/−55           | 362 +/− 75           |
| 4  | 364 +/− 129        | 370 +/− 73          | 335 +/− 85          | 278 +/− 100          |
| 7  | 388 +/− 108 (n = 9)| 404 +/− 93          | 363 +/− 104         | 185 +/− 79           |
| 11 | 447 +/− 124 (n = 9)| 405 +/− 160         | 458 +/− 95          | 206 +/− 98           |
| 14 | 472 +/− 119 (n = 8)| 379 +/− 139 (n = 8) | 501 +/− 87 (n = 7)  | 212 +/− 118          |
| 18 | 528 +/− 67 (n = 6) | 351 +/− 178 (n = 7) | 488 +/− 63 (n = 5)  | 200 +/− 129          |
| 21 | 533 +/− 66 (n = 4) | 285 +/− 151 (n = 6) | 469 +/− 6 (n = 2)   | 200 +/− 135          |
| 25 | 538 +/− 45 (n = 3) | 279 +/− 169 (n = 6) | 506 +/− 53 (n = 2)  | 163 +/− 39 (n = 9)   |
| 28 | 583 +/− 0 (n = 1)  | 204 +/− 95 (n = 5)  | 533 +/− 0 (n = 1)   | 150 +/− 23 (n = 9)   |
| 32 | 600 +/− 0 (n = 1)  | 221 +/− 101 (n = 5) | 600 +/− 0 (n = 1)   | 144 +/− 16 (n = 9)   |
| 35 | (n = 0)            | 205 +/− 116 (n = 5) | (n = 0)             | 143 +/− 15 (n = 9)   |
| 39 |                    | 224 +/− 140 (n = 5) |                     | 248 +/− 103 (n = 9)  |
| 42 |                    | 215 +/− 112 (n = 5) |                     | 204 +/− 61 (n = 9)   |
| 46 |                    | 201 +/− 122 (n = 5) |                     | 209 +/− 82 (n = 9)   |
| 49 |                    | 217 +/− 140 (n = 5) |                     | 157 +/− 33 (n = 9)   |
| 53 |                    | 229 +/− 186 (n = 5) |                     | 179 +/− 78 (n = 9)   |
| 56 |                    | 128 +/− 10 (n = 4)  |                     | 181 +/− 75 (n = 9)   |
| 60 |                    | 174 +/− 59 (n = 4)  |                     | 164 +/− 32 (n = 9)   |

TABLE 1-continued

Average blood glucose (mg/dL) +/− SD (standard deviation) following administration of liraglutide and/or anti-IL-21 in the NOD model (N = 10 per group at onset. Over the course of the experiment, some animals were removed from the study and euthanized due to high blood glucose values (above 600 mg/dL) and/or poor general health. Remaining n is indicated in the table). The time period shown runs through the liraglutide treatment phase (days 0-35 post diabetes onset) and an additional 35 days of monitoring. Limit of detection for the glucose meter was 600 mg/dL.

| Time (days post diabetes onset) | Untreated control | Treatment Anti-IL-21 alone | Liraglutide alone | Liraglutide and Anti-IL-21* |
|---|---|---|---|---|
| 63 | | 156 +/− 30 (n = 4) | | 191 +/− 52 (n = 9) |
| 67 | | 138 +/− 16 (n = 4) | | 167 +/− 51 (n = 9) |
| 70 | | 153 +/− 30 (n = 4) | | 192 +/− 82 (n = 9) |

*Liraglutide was only administered day 0-35 post diabetes onset.

The results are further illustrated by FIGS. 1 and 2 that clearly shows that none of the animals in group 1 or 2 survives during the 70 days. In contrast a much smaller number of mice are removed in treatment groups 3 and 4, with the combination treatment being most efficient as only one mouse was removed from the study during the 70 days period.

The data from this experiment show that mono-therapeutic treatment with anti-IL-21 is able to reverse hyperglycemia in some of the mice. Liraglutide mono-therapy, in line with previous experiments and the literature, does not affect progression to terminal hyperglycemia, although in the first days of dosing a significant yet temporary drop in blood glucose values was noted. It is only when the two treatments, i.e. anti-IL-21 and liraglutide, are combined that almost all animals experience lasting normalization of blood glucose levels. Interestingly, many treated animals remain normoglycemic upon withdrawal of liraglutide, suggesting expansion and/or recovery of functional beta-cell mass.

Example 2—Liraglutide in Combination with Anti-IL-21 in the NOD Model—Supplementary Data Enrolment of mice of as described in Example 1 was continued adding 9, 8, 8 and 8 subjects to the treatment groups 1 to 4, respectively. The average blood glucose measurements for the new subjects are included in Table 2, while the average blood glucose measurements for the complete data set is included in table 3.

In contrast to the above subjects these data include 3 untreated mice which were only transiently diabetic (low BGV lasting until day 70). This is unusual, but has been observed to occur with some frequency in particular if the mice are relatively old at diabetic onset. The average BGV for mice treated with anti-IL-21 alone is impacted by the removal of three "cured" mice (with low BGV), and therefore the average BGV of the remaining mice is higher than the result would have been if all mice were still included.

TABLE 2

(additional mice)

| Time (days post diabetes onset) | Untreated control | Anti-IL-21 alone | Liraglutide alone | Liraglutide and Anti-IL-21* |
|---|---|---|---|---|
| 0 | 312 +/− 52 (n = 9) | 353 +/− 59 (n = 8) | 373 +/− 85 (n = 8) | 315 +/− 55 (n = 8) |
| 4 | 329 +/− 85 (n = 9) | 326 +/− 104 (n = 8) | 199 +/− 66 (n = 8) | 198 +/− 101 (n = 8) |
| 7 | 347 +/− 91 (n = 9) | 375 +/− 103 (n = 8) | 203 +/− 119 (n = 8) | 150 +/− 20 (n = 8) |
| 11 | 372 +/− 129 (n = 9) | 361 +/− 125 (n = 8) | 306 +/− 133 (n = 8) | 173 +/− 49 (n = 8) |
| 14 | 414 +/− 159 (n = 9) | 338 +/− 153 (n = 8) | 363 +/− 152 (n = 8) | 172 +/− 61 (n = 8) |
| 18 | 305 +/− 111 (n = 6) | 336 +/− 183 (n = 8) | 402 +/− 157 (n = 7) | 156 +/− 21 (n = 8) |
| 21 | 335 +/− 122 (n = 6) | 248 +/− 153 (n = 6) | 396 +/− 169 (n = 6) | 158 +/− 69 (n = 8) |
| 28 | 443 +/− 139 (n = 5) | 219 +/− 162 (n = 6) | 413 +/− 210 (n = 5) | 172 +/− 67 (n = 8) |
| 35 | 305 +/− 179 (n = 4) | 147 +/− 15 (n = 5) | 178 +/− 22 (n = 2) | 167 +/− 62 (n = 8) |
| 42 | 198 +/− 19 (n = 3) | 264 +/− 121 (n = 2#) | 505 +/− 40 (n = 2) | 246 +/− 160 (n = 5#) |
| 49 | 244 +/− 81 (n = 3) | 118 +/− 17 (n = 2) | 503 +/− 63 (n = 2) | 271 +/− 145 (n = 5) |
| 56 | 203 +/− 47 (n = 3) | 286 +/− 107 (n = 2) | 476 +/− 0 (n = 1) | 279 +/− 177 (n = 5) |
| 63 | 196 +/− 67 (n = 3) | 314 +/− 157 (n = 2) | 600 +/− 0 (n = 1) | 190 +/− 81 (n = 4) |
| 70 | 208 +/− 50 (n = 3) | 400 +/− 108 (n = 2) | (n = 0) | 256 +/− 137 (n = 4) |

*Liraglutide was only administered day 0-35 post diabetes onset.
Three mice were taken for histology samples at day 35 from the Anti-IL-21 alone and liraglutide + Anti-Il-21 groups and the reduction in n from 5 to 2 and 8 to 5 does thus not reflect removal of mice due to high BGV or poor general health.

Example 3—Liraglutide in Combination with Anti-IL-21 in the NOD Model Compilation of Data from Example 1 and Example 2

All data from example 1 and example 2 has been compiled to provide data for a total of 19, 18, 18 and 18 subjects in the four treatments groups as described in the table here below.

| Group | n | Treatment | Dosing Regimen |
|---|---|---|---|
| 1 | 19 | Untreated | No treatment |
| 2 | 18 | Anti-IL-21 alone | 5 doses of anti-IL-21 at 25 mg/kg BW, i.p. 2x/week for 2.5 weeks Beginning at diabetes onset |
| 3 | 18 | Liraglutide alone | 0.3 mg/kg BW on day 0, s.c. 0.6 mg/kg BW on day 1, s.c. 1 mg/kg BW from day 2-34, s.c. Beginning at diabetes onset, 35 doses total |
| 4 | 18 | Anti-IL-21 + liraglutide | Dosed as above for each monotherapy |

The average BGV values are included in table 3, as above.

The average BGV values for all mice of example 1 and 2 are illustrated in FIGS. 3 and 4, again showing that the number of mice surviving in the untreated and liraglutide treated groups is very small, while a substantial number of mice treated with anti-IL-21 either alone or in combination with liraglutide remained viable throughout the study period of 70 days. Again the removal of three animals in these two groups results in the representation being not completely in line with the actual effect.

each group. It is seen that the n for anti-IL-21 and the combination treatment is 15 (and not 18) to account for the 3+3 mice that were removed for histological examination. Again the combination treatment was effective as only 2 mice out of 15 were sacrificed due to being terminally hyperglycemic or of general poor health. It is also noted that only 3 and 0 animal untreated and liraglutide treated, respectively, did not become terminally hyperglycaemic by day 70.

Histological examination: The histological analyses were performed on pancreatic tissue from a subset of mice from each group. Sections were stained with Hematoxylin and eosin (H&E) to assess insulitis and immunofluorescent staining with either CD8 and insulin or CD4 and insulin to assess insulitis and also characterize cell types within infiltrates. Untreated mice and mice treated with liraglutide had few visible islets remaining (as expected in mice that had become terminally hyperglycaemic (BGV>600 mg/dL). The pancreas from these mice exhibited heavy cellular infiltration, whereas mice treated with Anti-IL-21 alone or in combination with liraglutide showed a decreased extent of infiltration. Insulitis was reduced in surviving mice treated with anti-IL-21 alone or in combination with liraglutide.

TABLE 3

(all mice)

| | Treatment | | | |
|---|---|---|---|---|
| Time (days post diabetes onset) | Untreated control | Anti-IL-21 alone | Liraglutide alone | Liraglutide and Anti-IL-21* |
| 0 | 345 +/− 81 (n = 19) | 352 +/− 57 (n = 18) | 373 +/− 70 (n = 18) | 341 +/− 71 (n = 18) |
| 4 | 347 +/− 111 (n = 19) | 351 +/− 91 (n = 18) | 274 +/− 102 (n = 18) | 242 +/− 108 (n = 18) |
| 7 | 368 +/− 102 (n = 18) | 391 +/− 99 (n = 18) | 292 +/− 136 (n = 18) | 169 +/− 63 (n = 18) |
| 11 | 410 +/− 132 (n = 18) | 385 +/− 147 (n = 18) | 391 +/− 136 (n = 18) | 191 +/− 82 (n = 18) |
| 14 | 441 +/− 127 (n = 17) | 358 +/− 148 (n = 16) | 427 +/− 144 (n = 15) | 194 +/− 99 (n = 18) |
| 18 | 427 +/− 143 (n = 11) | 343 +/− 181 (n = 15) | 438 +/− 133 (n = 13) | 181 +/− 100 (n = 18) |
| 21 | 414 +/− 142 (n = 10) | 267 +/− 153 (n = 12) | 414 +/− 150 (n = 8) | 181 +/− 113 (n = 18) |
| 28 | 466 +/− 137 (n = 6) | 212 +/− 136 (n = 11) | 433 +/− 197 (n = 6) | 160 +/− 50 (n = 17) |
| 35 | 305 +/− 179 (n = 4) | 176 +/− 88 (n = 10) | 178 +/− 22 (n = 2) | 154 +/− 46 (n = 17) |
| 42 | 198 +/− 19 (n = 3) | 229 +/− 117 (n = 7#) | 505 +/− 40 (n = 2) | 219 +/− 109 (n = 14#) |
| 49 | 244 +/− 81 (n = 3) | 189 +/− 127 (n = 7) | 503 +/− 63 (n = 2) | 198 +/− 106 (n = 14) |
| 56 | 203 +/− 47 (n = 3) | 181 +/− 97 (n = 6) | 476 +/− 0 (n = 1) | 216 +/− 130 (n = 14) |
| 63 | 196 +/− 67 (n = 3) | 209 +/− 119 (n = 6) | 600 +/− 0 (n = 1) | 190 +/− 63 (n = 13) |
| 70 | 208 +/− 50 (n = 3) | 236 +/− 134 (n = 6) | (n = 0) | 212 +/− 106 (n = 13) |

*Liraglutide was only administered day 0-35 post diabetes onset.
Three mice were taken for histology samples at day 35 from the Anti-IL-21 alone and liraglutide + Anti-Il-21 groups and the reduction in n from 5 to 2 and 8 to 5 does thus not reflect removal of mice due to high BGV or poor general health.

To evaluate the results, the average BGV values must be combined with the number of mice participating and remaining in the study relative to the number of mice that are removed during the study due to being terminally ill. This is illustrated by Kaplan-Meyer plots of FIG. 5. The upper graph (FIG. 5A) illustrates the fraction (percentage) of mice that remain diabetic e.g. mice with a BGV above 250 and include mice that are removed from the study due to a BGV above 600 or poor general health. Not surprisingly only few untreated or liraglutide treated mice recover spontaneously during the 35 days period. In contrast treatment with anti-IL-21 is able to reverse diabetes (lowering BGV to below 250 mg/mL) in half of the mice and in combination with liraglutide only 2 (out of 18) mice remained diabetic during the first 35 days of the study, representing the treatment period.

The lower graph (FIG. 5B) illustrates the survival rate in each treatment group defined by the number of mice remaining in the study for the full period (70 days), relative to n in Example 4—Liraglutide in Combination with Anti-IL-21 in the NOD Model—Confirmation Study The study is performed as described for example 1 with the treatment groups as described in the table here below.

| Group | n | Treatment | Dosing Regimen |
|---|---|---|---|
| 1 | 10 | Untreated | No treatment |
| 2 | 16 | Anti-IL-21 alone | 5 doses of Anti-IL-21 at 25 mg/kg BW, i.p. 2x/week for 2.5 weeks Beginning at diabetes onset |
| 3 | 10 | Liraglutide alone | 0.3 mg/kg BW on day 0, s.c. 0.6 mg/kg BW on day 1, s.c. 1 mg/kg BW from day 2-34, s.c. Beginning at diabetes onset, 35 doses total |

-continued

| Group | n | Treatment | Dosing Regimen |
|---|---|---|---|
| 4 | 15 | Anti-IL-21 + liraglutide | Dosed as above for each monotherapy Beginning at diabetes onset |

Detailed data are not included here, as the overall results are in agreement with the earlier study.

Brief description: The Anti-IL-21 monotherapy successfully cured 75% of the mice with established hyperglycaemia in the first 35 days post disease onset, while liraglutide alone had little effect on diabetes progression, with 60% of mice becoming terminally hyperglycaemic before the end of the liraglutide treatment period, and the remaining 40% shortly thereafter.

However, when Anti-IL-21 and liraglutide were administered in combination, this regimen reversed established hyperglycaemia in 87% of treated mice, and also resulted in enhanced survival compared to untreated mice and those treated with liraglutide alone through 70 days post onset of hyperglycaemia (80% survival for combination therapy; 0% for both liraglutide alone and untreated). Anti-IL-21 monotherapy also provided enhanced survival (75%) compared to untreated and mice treated with liraglutide alone.

The data demonstrate that combination therapy with Anti-IL-21 plus liraglutide provides enhanced efficacy compared to monotherapy with either agent in reversing established diabetes. This return to normoglycaemia remains stable for the majority of the mice even after liraglutide is withdrawn.

The invention claimed is:

1. A composition comprising a GLP-1 agonist and an inhibitor of IL-21 function, wherein said inhibitor of IL-21 function is an antibody that is capable of specifically binding IL-21.

2. The composition according to claim 1, wherein said antibody binds to
   a. helix 1 and 3 of human IL-21, or
   b. helix 2 and 4 of human IL-21.

3. The composition according to claim 1, wherein said antibody binds to a discontinuous epitope on IL-21, wherein said epitope comprises amino acids I37 to Y52 and N92 to P108 as set forth in SEQ ID NO 1.

4. The composition according to claim 1, wherein said antibody comprises
   c. the three CDR sequences as set forth in SEQ ID NO: 2 and the three CDR sequences as set forth in SEQ ID NO: 3, or
   d. the three CDR sequences as set forth in SEQ ID NO: 2 and the three CDR sequences as set forth in SEQ ID NO: 3 except that heavy chain CDR1 is TYGMH,
   e. the three CDR sequences as set forth in SEQ ID NO: 4 and the three CDR sequences as set forth in SEQ ID NO: 5.

5. The composition according to claim 1, wherein said antibody specifically binds to IL-21 with a binding affinity of $10^7 M^{-1}$ or greater, $10^8 M^{-1}$ or greater, $10^9 M^{-1}$ or greater, $10^{10} M^{-1}$ or greater, $10^{10} M^{-1}$ or greater, or $10^{12} M^{-1}$ or greater.

6. The composition according to claim 1, wherein said GLP-1 agonist is a GLP-1 peptide.

7. The composition according to claim 1, wherein said GLP-1 agonist is a GLP-1 derivative.

8. The composition according to claim 1, wherein said GLP-1 agonist is an albumin binding GLP-1 derivative.

9. The composition according to claim 8, wherein said albumin binding GLP-1 derivative is a fatty acid GLP-1 derivative.

10. The composition according to claim 8, wherein said albumin binding GLP-1 derivative comprises an albumin binding moiety attached via a Lys residue to a GLP-1 peptide.

11. The composition according to claim 10, wherein the Lys residue is at position 23, 26, 34, or 36 relative to the amino acid sequence of GLP-1 (7-37) of SEQ ID NO: 8.

12. The composition according to claim 1, wherein said GLP-1 agonist is liraglutide.

13. The composition according to claim 1, wherein said GLP-1 agonist, and said inhibitor of IL-21 function are administered concomitantly or sequentially.

14. The composition according to claim 1, further comprising an additional excipient.

15. A method for treating type 1 diabetes, comprising administering an effective amount of a GLP-1 agonist and an inhibitor of IL-21 function to a patient in need thereof, wherein said inhibitor of IL-21 function is an antibody that is capable of specifically binding IL-21.

* * * * *